(12) United States Patent
Ko

(10) Patent No.: US 12,098,392 B2
(45) Date of Patent: Sep. 24, 2024

(54) COMPOSITIONS AND METHODS FOR DIFFERENTIATION OF HUMAN PLURIPOTENT STEM CELLS INTO DESIRED CELL TYPES

(71) Applicant: Elixirgen Scientific, Inc, Baltimore, MD (US)

(72) Inventor: Minoru S. H. Ko, Baltimore, MD (US)

(73) Assignee: ELIXIRGEN SCIENTIFIC, INC., Baltimore, MD (US)

(*) Notice: Subject to any disclaimer, the term of this patent is extended or adjusted under 35 U.S.C. 154(b) by 258 days.

(21) Appl. No.: 17/458,609

(22) Filed: Aug. 27, 2021

(65) Prior Publication Data

US 2021/0395699 A1    Dec. 23, 2021

Related U.S. Application Data

(62) Division of application No. 15/905,982, filed on Feb. 27, 2018, now Pat. No. 11,136,555.

(60) Provisional application No. 62/523,324, filed on Jun. 22, 2017, provisional application No. 62/465,188, filed on Mar. 1, 2017.

(51) Int. Cl.
| | |
|---|---|
| *C12N 5/0793* | (2010.01) |
| *C07K 14/00* | (2006.01) |
| *C12N 5/071* | (2010.01) |
| *C12N 5/074* | (2010.01) |
| *C12N 5/077* | (2010.01) |
| *C12N 5/0789* | (2010.01) |
| *C12N 15/113* | (2010.01) |
| *C12N 15/85* | (2006.01) |
| *C12N 15/86* | (2006.01) |

(52) U.S. Cl.
CPC ............ *C12N 5/0696* (2013.01); *C07K 14/00* (2013.01); *C12N 5/0619* (2013.01); *C12N 5/0647* (2013.01); *C12N 5/0658* (2013.01); *C12N 5/067* (2013.01); *C12N 15/113* (2013.01); *C12N 15/85* (2013.01); *C12N 15/86* (2013.01); *C12N 2015/8518* (2013.01); *C12N 2310/14* (2013.01); *C12N 2501/60* (2013.01); *C12N 2501/602* (2013.01); *C12N 2501/603* (2013.01); *C12N 2506/02* (2013.01); *C12N 2506/03* (2013.01); *C12N 2506/08* (2013.01); *C12N 2506/1323* (2013.01); *C12N 2506/14* (2013.01); *C12N 2506/45* (2013.01); *C12N 2510/00* (2013.01); *C12N 2523/00* (2013.01); *C12N 2760/18741* (2013.01); *C12N 2760/18843* (2013.01); *C12N 2800/107* (2013.01)

(58) Field of Classification Search
CPC ............. C12N 5/0619; C12N 2506/02; C12N 2506/03; C12N 2506/45
See application file for complete search history.

(56) References Cited

U.S. PATENT DOCUMENTS

| | | |
|---|---|---|
| 10,335,456 B2 | 7/2019 | Ko |
| 2013/0302893 A1 | 11/2013 | Pei et al. |
| 2014/0370537 A1 | 12/2014 | Sakurai et al. |
| 2015/0275171 A1 | 10/2015 | Kato et al. |
| 2016/0010056 A1 | 1/2016 | Nakaki et al. |
| 2018/0072988 A1* | 3/2018 | Sun .................. C12N 5/0619 |
| 2018/0251735 A1 | 9/2018 | Ko |

FOREIGN PATENT DOCUMENTS

| | | | |
|---|---|---|---|
| EP | 3050961 A1 | 8/2016 | |
| JP | 2009-045004 A | 3/2009 | |
| WO | WO-2016163958 A1 * | 10/2016 | ............ C12N 15/85 |
| WO | 2017073763 A1 | 5/2017 | |
| WO | 2017131238 A1 | 8/2017 | |

OTHER PUBLICATIONS

Ban et al. PNAS 108(34):14234-14239, 2011 (Year: 2011).*
International Search Report and Written Opinion issued in corresponding International Patent Application No. PCT/JP2016/082152 dated Jan. 24, 2017 (7 pages).
Akiyama et al., "Transient ectopic expression of the histone demethylase JMJD3 accelerates the differentiation of human pluripotent stem cells," Development, 2016, pp. 3674-3685, vol. 143.
Correa-Cerro et al., "Generation of mouse ES cell lines engineered for the forced induction of transcription factors," Scientific Reports, 2011, pp. 1-6, vol. 1, No. 167.
Dey et al., "The Histone Demethylase KDM5b/JARID1b Plays a Role in Cell Fate Decisions by Blocking Terminal Differentiation," Molecular And Cellular Biology, 2008, pp. 5312-5532, vol. 28, No. 17.
Goto, "Analysis of time-dependent fate control mechanism of neural stem cells," Research Reports of Uehara Memorial Foundation, 2008, pp. 1-3, p. 1, vol. 22 (machine translation attached).
Nishiyama et al., "Uncovering Early Response of Gene Regulatory Networks in ESCs by Systematic Induction of Transcription Factors," Cell Stem Cell, 2009, pp. 420-433, vol. 5.

(Continued)

*Primary Examiner* — Marcia S Noble
(74) *Attorney, Agent, or Firm* — Kilyk & Bowersox, P.L.L.C.

(57) ABSTRACT

In related-art methods of differentiating pluripotent stem cells into a desired cell type, there has not been established a differentiation induction method using human ES/iPS cells and being stable and highly efficient. The use of complicated culture steps is a large problem. In addition, there are also large problems in, for example, that the speed of cell differentiation is low, and hence long-period culture is required, and that the differentiation efficiency is low, and hence it is difficult to obtain a sufficient number of required cells. A method of inducing differentiation into a desired cell type, which induces differentiation within a short period of time and with high efficiency by the use of a Sendai virus vector capable of expressing a transcription factor, and as required, the use of a pluripotent stem cell in which an expression amount of a POU5F1 protein has been substantially removed or reduced, is provided.

4 Claims, 3 Drawing Sheets
(3 of 3 Drawing Sheet(s) Filed in Color)
Specification includes a Sequence Listing.

(56) References Cited

OTHER PUBLICATIONS

Torres et al., "Utx Is Required for Proper Induction of Ectoderm and Mesoderm during Differentiation of Embryonic Stem Cells," PLOS ONE, 2013, pp. 1-15, vol. 8, Issue 4.
Wang et al., "Histone demethylase KDM2B inhibits the chondrogenic differentiation potentials of stem cells from apical papilla," Int. J. Clin. Exp. Med., 2015, pp. 2165-2173, vol. 8, No. 2.
Xiang, "JMJD3 is a histone H3K27 demethylase," Cell Research, 2007, pp. 850-857, vol. 17.
Yamamizu et al., "Identification of Transcription Factors for Lineage-Specific ESC Differentiation," Stem Cell Reports, 2013, pp. 1-15, vol. 1.
Yamamizu et al., "Development of a differentiation induction method from pluripotent stem cells to arbitrary cells using transcription factor," Experimental Medicine, 2015, pp. 239-246, p. 242, vol. 33, No. 2 (machine translation attached).
Zasshi, "Establishment of a Method of Hepatocyte Differentiation from Human Pluripotent Stem Cells for Innovation Drug Development," 2015, pp. 1141-1146, p. 1142, vol. 135, No. 10 (machine translation attached).
Ban et al., "Efficient generation of transgene-free human induced pluripotent stem cells (iPSCs) by temperature-sensitive Sendai virus vectors," PNAS, 2011, vol. 108, No. 34, pp. 14234-14239.
Busskamp et al., "Rapid neurogenesis through transcriptional activation in human stem cells," Molecular Systems Biology, 2014, 10:760, pp. 1-21.
Chambers et al., "Combined small molecule inhibition accelerates developmental timing and converts human pluripotent stem cells into nociceptors," 2013, Nat Biotechnol., 30(7), pp. 715-720 (pp. 1-17).
Goparaju et al., "Rapid differentiation of human pluripotent stem cells into functional neurons by mRNAs encoding transcription factors," Scientific Reports, 2017, 7:42367, pp. 1-12.
Hay et al., "Efficient Differentiation of Hepatocytes from Human Embryonic Stem Cells Exhibiting Markers Recapitulating Liver Development In Vivo," Stem Cells, 2008, 26, pp. 894-902.
Hester et al., "Rapid and Efficient Generation of Functional Motor Neurons From Human Pluripotent Stem Cells Using Gene Delivered Transcription Factor Codes," Molecular Therapy, 2011, vol. 19, No. 10, pp. 1905-1912.
Hirayama et al., "Identification of transcription factors that promote the differentiation of human pluripotent stem cells into lacrimal gland epithelium-like cells," npj Aging and Mechanisms of Disease, 2017, 3:1, pp. 1-9.
Hu et al., "Neural differentiation of human induced pluripotent stem cells follows developmental principles but with variable potency," PNAS, 2010, vol. 107, No. 9, pp. 4335-4340.
Inoue et al., "Nontransmissible Virus-Like Particle Formation by F-Deficient Sendai Virus Is Temperature Sensitive and Reduced by Mutations in M and HN Proteins," Journal of Virology, 2003, vol. 77, No. 5, pp. 3238-3246.
Kajiwara et al., "Donor-dependent variations in hepatic differentiation from human-induced pluripotent stem cells," PNAS, 2012, vol. 109, No. 31, pp. 12538-12543.
Paris et al., "Conjugating Phosphospermines to siRNAs for Improved Stability in Serum, Intracellular Delivery and RNAi-Mediated Gene Silencing," Molecular Pharmaceutics, 2012, vol. 9, pp. 3464-3475.
Warren et al., "Highly efficient reprogramming to pluripotency and directed differentiation of human cells using synthetic modified mRNA," Cell Stem Cell, 2010, 7(5), pp. 618-630 (pp. 1-23).
Woltjen et al., "piggyBac transposition reprograms fibroblasts to induced pluripotent stem cells," Nature, 2009, 458 (7239), pp. 766-770 (pp. 1-13).
Zhang et al., "Rapid Single-Step Induction of Functional Neurons from Human Pluripotent Stem Cells," Neuron, 2013, 78(5), pp. 785-798 (pp. 1-24).
Tadaka et al. "Efficient gene silencing and cell differentiation using siRNA in mouse and monkey ES cells," Biochemical and Biophysical Research Communications, 331(4): 1039-1044, 2005 (Year: 2005).
Bitzer et al. "Sendai virus vectors as an emerging negative-strand RNA viral vector system," J. Gene Med 2003, 5:543-553 (Year: 2003).

* cited by examiner

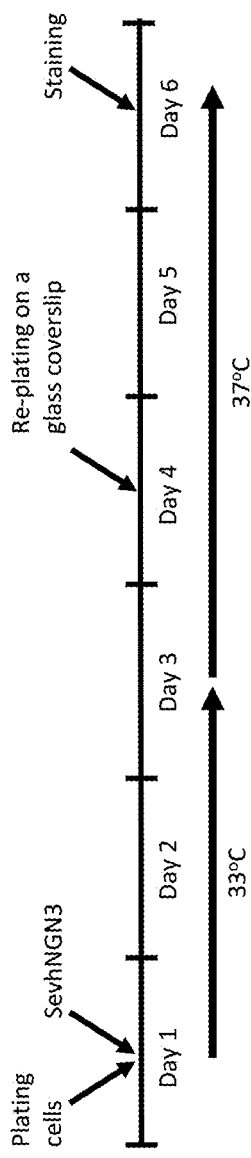
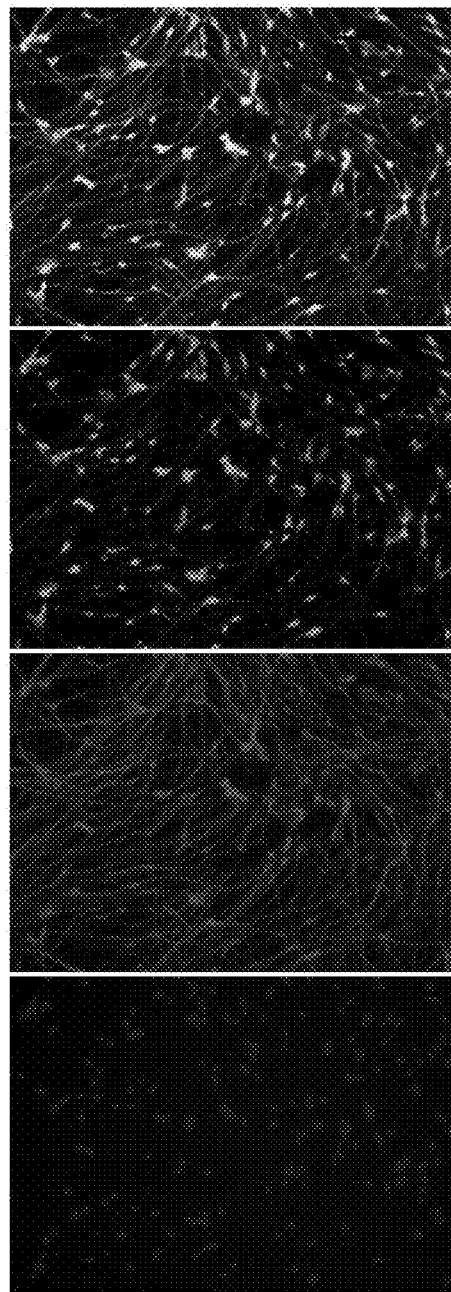

SEQUENCE LISTING

<160> NUMBER OF SEQ ID NOS: 19

<210> SEQ ID NO 1
<211> LENGTH: 360
<212> TYPE: PRT
<213> ORGANISM: Homo sapiens

<400> SEQUENCE: 1

```
Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270
```

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 2
<211> LENGTH: 1083
<212> TYPE: DNA
<213> ORGANISM: Homo sapiens

<400> SEQUENCE: 2
atggcgggac acctggcttc ggatttcgcc ttctcgcccc ctccaggtgg tggaggtgat    60
gggccagggg ggccggagcc gggctgggtt gatcctcgga cctggctaag cttccaaggc   120
cctcctggag ggccaggaat cgggccgggg gttgggccag gctctgaggt gtggggggatt  180
cccccatgcc cccgccgta tgagttctgt gggggggatgg cgtactgtgg gccccaggtt   240
ggagtggggc tagtgcccca aggcggcttg gagacctctc agcctgaggg cgaagcagga   300
gtcggggtgg agagcaactc cgatggggcc tccccggagc cctgcaccgt caccccctggt  360
gccgtgaagc tggagaagga aagctggag caaaacccgg aggagtccca ggacatcaaa    420
gctctgcaga agaactcga gcaatttgcc aagctcctga gcagaagag gatcaccctg     480
ggatatacac aggccgatgt ggggctcacc ctgggggttc tatttgggaa ggtattcagc   540
caaacgacca tctgccgctt tgaggctctg cagcttagct tcaagaacat gtgtaagctg   600
cggcccttgc tgcagaagtg ggtggaggaa gctgacaaca atgaaaatct tcaggagata   660
tgcaaagcag aaaccctcgt gcaggcccga agagaaagc gaaccagtat cgagaaccga   720
gtgagaggca acctggagaa tttgttcctg cagtgcccga aacccacact gcagcagatc   780
agccacatcg cccagcagct tgggctcgag aaggatgtgg tccgagtgtg gttctgtaac   840
cggcgccaga agggcaagcg atcaagcagc gactatgcac aacgagagga ttttgaggct   900
gctgggtctc ctttctcagg gggaccagtg tcctttcctc tggccccagg gccccatttt   960
ggtaccccag gctatgggag ccctcacttc actgcactgt actcctcggt cccttttcct  1020
gaggggaag cctttccccc tgtctccgtc accactctgg gctctcccat gcattcaaac  1080
tga                                                                1083

<210> SEQ ID NO 3
<211> LENGTH: 1682
<212> TYPE: PRT
<213> ORGANISM: Homo sapiens

<400> SEQUENCE: 3

Met His Arg Ala Val Asp Pro Pro Gly Ala Arg Ala Ala Arg Glu Ala
1               5                   10                  15

Phe Ala Leu Gly Gly Leu Ser Cys Ala Gly Ala Trp Ser Ser Cys Pro
            20                  25                  30

```
Pro His Pro Pro Pro Arg Ser Ala Trp Leu Pro Gly Gly Arg Cys Ser
        35                  40                  45

Ala Ser Ile Gly Gln Pro Pro Leu Pro Ala Pro Leu Pro Pro Ser His
 50                  55                  60

Gly Ser Ser Ser Gly His Pro Ser Lys Pro Tyr Tyr Ala Pro Gly Ala
 65                  70                  75                  80

Pro Thr Pro Arg Pro Leu His Gly Lys Leu Glu Ser Leu His Gly Cys
                 85                  90                  95

Val Gln Ala Leu Leu Arg Glu Pro Ala Gln Pro Gly Leu Trp Glu Gln
                100                 105                 110

Leu Gly Gln Leu Tyr Glu Ser Glu His Asp Ser Glu Glu Ala Thr Arg
        115                 120                 125

Cys Tyr His Ser Ala Leu Arg Tyr Gly Gly Ser Phe Ala Glu Leu Gly
        130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
        210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Leu Pro Pro Pro Pro Pro Pro
                245                 250                 255

Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
        275                 280                 285

Ala Trp Gly Pro Glu Arg Lys Gly Ser Ala Pro Pro Glu Arg Gln Glu
        290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335

Pro Gly Pro Arg Pro Pro Gly Ala Glu Ser His Gly Cys Leu Pro Ala
            340                 345                 350

Thr Arg Pro Pro Gly Ser Asp Leu Arg Glu Ser Arg Val Gln Arg Ser
        355                 360                 365

Arg Met Asp Ser Ser Val Ser Pro Ala Ala Thr Thr Ala Cys Val Pro
        370                 375                 380

Tyr Ala Pro Ser Arg Pro Pro Gly Leu Pro Gly Thr Thr Ser Ser
385                 390                 395                 400

Ser Ser Ser Ser Ser Asn Thr Gly Leu Arg Gly Val Glu Pro Asn
                405                 410                 415

Pro Gly Ile Pro Gly Ala Asp His Tyr Gln Thr Pro Ala Leu Glu Val
            420                 425                 430

Ser His His Gly Arg Leu Gly Pro Ser Ala His Ser Ser Arg Lys Pro
        435                 440                 445
```

```
Phe Leu Gly Ala Pro Ala Ala Thr Pro His Leu Ser Leu Pro Pro Gly
    450                 455                 460

Pro Ser Ser Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
                485                 490                 495

Asp Gly Glu Ile Leu Glu Glu Leu Phe Phe Gly Thr Glu Gly Pro Pro
                500                 505                 510

Arg Pro Ala Pro Pro Leu Pro His Arg Glu Gly Phe Leu Gly Pro
    515                 520                 525

Pro Ala Ser Arg Phe Ser Val Gly Thr Gln Asp Ser His Thr Pro Pro
    530                 535                 540

Thr Pro Pro Thr Pro Thr Thr Ser Ser Asn Ser Asn Ser Gly Ser
545                 550                 555                 560

His Ser Ser Ser Pro Ala Gly Pro Val Ser Phe Pro Pro Pro Tyr
                565                 570                 575

Leu Ala Arg Ser Ile Asp Pro Leu Pro Arg Pro Pro Ser Pro Ala Gln
                580                 585                 590

Asn Pro Gln Asp Pro Pro Leu Val Pro Leu Thr Leu Ala Leu Pro Pro
    595                 600                 605

Ala Pro Pro Ser Ser Cys His Gln Asn Thr Ser Gly Ser Phe Arg Arg
    610                 615                 620

Pro Glu Ser Pro Arg Pro Arg Val Ser Phe Pro Lys Thr Pro Glu Val
625                 630                 635                 640

Gly Pro Gly Pro Pro Gly Pro Leu Ser Lys Ala Pro Gln Pro Val
                645                 650                 655

Pro Pro Gly Val Gly Glu Leu Pro Ala Arg Gly Pro Arg Leu Phe Asp
                660                 665                 670

Phe Pro Pro Thr Pro Leu Glu Asp Gln Phe Glu Glu Pro Ala Glu Phe
            675                 680                 685

Lys Ile Leu Pro Asp Gly Leu Ala Asn Ile Met Lys Met Leu Asp Glu
        690                 695                 700

Ser Ile Arg Lys Glu Glu Glu Gln Gln His Glu Ala Gly Val Ala
705                 710                 715                 720

Pro Gln Pro Pro Leu Lys Glu Pro Phe Ala Ser Leu Gln Ser Pro Phe
                725                 730                 735

Pro Thr Asp Thr Ala Pro Thr Thr Ala Pro Ala Val Ala Val Thr
            740                 745                 750

Thr Thr Thr Thr Thr Thr Thr Thr Ala Thr Gln Glu Glu Glu
            755                 760                 765

Lys Lys Pro Pro Ala Leu Pro Pro Pro Pro Leu Ala Lys Phe
    770                 775                 780

Pro Pro Pro Ser Gln Pro Gln Pro Pro Pro Pro Pro Ser Pro
785                 790                 795                 800

Ala Ser Leu Leu Lys Ser Leu Ala Ser Val Leu Glu Gly Gln Lys Tyr
                805                 810                 815

Cys Tyr Arg Gly Thr Gly Ala Ala Val Ser Thr Arg Pro Gly Pro Leu
                820                 825                 830

Pro Thr Thr Gln Tyr Ser Pro Gly Pro Pro Ser Gly Ala Thr Ala Leu
            835                 840                 845

Pro Pro Thr Ser Ala Ala Pro Ser Ala Gln Gly Ser Pro Gln Pro Ser
        850                 855                 860
```

-continued

```
Ala Ser Ser Ser Ser Gln Phe Ser Thr Ser Gly Gly Pro Trp Ala Arg
865                 870                 875                 880

Glu Arg Arg Ala Gly Glu Glu Pro Val Pro Gly Pro Met Thr Pro Thr
                885                 890                 895

Gln Pro Pro Pro Pro Leu Ser Leu Pro Pro Ala Arg Ser Glu Ser Glu
            900                 905                 910

Val Leu Glu Glu Ile Ser Arg Ala Cys Glu Thr Leu Val Glu Arg Val
        915                 920                 925

Gly Arg Ser Ala Thr Asp Pro Ala Asp Pro Val Asp Thr Ala Glu Pro
    930                 935                 940

Ala Asp Ser Gly Thr Glu Arg Leu Leu Pro Pro Ala Gln Ala Lys Glu
945                 950                 955                 960

Glu Ala Gly Gly Val Ala Ala Val Ser Gly Ser Cys Lys Arg Arg Gln
                965                 970                 975

Lys Glu His Gln Lys Glu His Arg Arg His Arg Arg Ala Cys Lys Asp
            980                 985                 990

Ser Val Gly Arg Arg Pro Arg Glu Gly Arg Ala Lys Ala Lys Ala Lys
        995                 1000                1005

Val Pro Lys Glu Lys Ser Arg Arg Val Leu Gly Asn Leu Asp Leu
    1010                1015                1020

Gln Ser Glu Glu Ile Gln Gly Arg Glu Lys Ser Arg Pro Asp Leu
    1025                1030                1035

Gly Gly Ala Ser Lys Ala Lys Pro Pro Thr Ala Pro Ala Pro Pro
    1040                1045                1050

Ser Ala Pro Ala Pro Ser Ala Gln Pro Thr Pro Ser Ala Ser
    1055                1060                1065

Val Pro Gly Lys Lys Ala Arg Glu Glu Ala Pro Gly Pro Pro Gly
    1070                1075                1080

Val Ser Arg Ala Asp Met Leu Lys Leu Arg Ser Leu Ser Glu Gly
    1085                1090                1095

Pro Pro Lys Glu Leu Lys Ile Arg Leu Ile Lys Val Glu Ser Gly
    1100                1105                1110

Asp Lys Glu Thr Phe Ile Ala Ser Glu Val Glu Glu Arg Arg Leu
    1115                1120                1125

Arg Met Ala Asp Leu Thr Ile Ser His Cys Ala Ala Asp Val Val
    1130                1135                1140

Arg Ala Ser Arg Asn Ala Lys Val Lys Gly Lys Phe Arg Glu Ser
    1145                1150                1155

Tyr Leu Ser Pro Ala Gln Ser Val Lys Pro Lys Ile Asn Thr Glu
    1160                1165                1170

Glu Lys Leu Pro Arg Glu Lys Leu Asn Pro Pro Thr Pro Ser Ile
    1175                1180                1185

Tyr Leu Glu Ser Lys Arg Asp Ala Phe Ser Pro Val Leu Leu Gln
    1190                1195                1200

Phe Cys Thr Asp Pro Arg Asn Pro Ile Thr Val Ile Arg Gly Leu
    1205                1210                1215

Ala Gly Ser Leu Arg Leu Asn Leu Gly Leu Phe Ser Thr Lys Thr
    1220                1225                1230

Leu Val Glu Ala Ser Gly Glu His Thr Val Glu Val Arg Thr Gln
    1235                1240                1245

Val Gln Gln Pro Ser Asp Glu Asn Trp Asp Leu Thr Gly Thr Arg
    1250                1255                1260
```

```
Gln Ile Trp Pro Cys Glu Ser Ser Arg Ser His Thr Thr Ile Ala
1265                 1270                1275

Lys Tyr Ala Gln Tyr Gln Ala Ser Ser Phe Gln Glu Ser Leu Gln
1280                 1285                1290

Glu Glu Lys Glu Ser Glu Asp Glu Glu Ser Glu Glu Pro Asp Ser
1295                 1300                1305

Thr Thr Gly Thr Pro Pro Ser Ser Ala Pro Asp Pro Lys Asn His
1310                 1315                1320

His Ile Ile Lys Phe Gly Thr Asn Ile Asp Leu Ser Asp Ala Lys
1325                 1330                1335

Arg Trp Lys Pro Gln Leu Gln Glu Leu Leu Lys Leu Pro Ala Phe
1340                 1345                1350

Met Arg Val Thr Ser Thr Gly Asn Met Leu Ser His Val Gly His
1355                 1360                1365

Thr Ile Leu Gly Met Asn Thr Val Gln Leu Tyr Met Lys Val Pro
1370                 1375                1380

Gly Ser Arg Thr Pro Gly His Gln Glu Asn Asn Asn Phe Cys Ser
1385                 1390                1395

Val Asn Ile Asn Ile Gly Pro Gly Asp Cys Glu Trp Phe Ala Val
1400                 1405                1410

His Glu His Tyr Trp Glu Thr Ile Ser Ala Phe Cys Asp Arg His
1415                 1420                1425

Gly Val Asp Tyr Leu Thr Gly Ser Trp Trp Pro Ile Leu Asp Asp
1430                 1435                1440

Leu Tyr Ala Ser Asn Ile Pro Val Tyr Arg Phe Val Gln Arg Pro
1445                 1450                1455

Gly Asp Leu Val Trp Ile Asn Ala Gly Thr Val His Trp Val Gln
1460                 1465                1470

Ala Thr Gly Trp Cys Asn Asn Ile Ala Trp Asn Val Gly Pro Leu
1475                 1480                1485

Thr Ala Tyr Gln Tyr Gln Leu Ala Leu Glu Arg Tyr Glu Trp Asn
1490                 1495                1500

Glu Val Lys Asn Val Lys Ser Ile Val Pro Met Ile His Val Ser
1505                 1510                1515

Trp Asn Val Ala Arg Thr Val Lys Ile Ser Asp Pro Asp Leu Phe
1520                 1525                1530

Lys Met Ile Lys Phe Cys Leu Leu Gln Ser Met Lys His Cys Gln
1535                 1540                1545

Val Gln Arg Glu Ser Leu Val Arg Ala Gly Lys Lys Ile Ala Tyr
1550                 1555                1560

Gln Gly Arg Val Lys Asp Glu Pro Ala Tyr Tyr Cys Asn Glu Cys
1565                 1570                1575

Asp Val Glu Val Phe Asn Ile Leu Phe Val Thr Ser Glu Asn Gly
1580                 1585                1590

Ser Arg Asn Thr Tyr Leu Val His Cys Glu Gly Cys Ala Arg Arg
1595                 1600                1605

Arg Ser Ala Gly Leu Gln Gly Val Val Val Leu Glu Gln Tyr Arg
1610                 1615                1620

Thr Glu Glu Leu Ala Gln Ala Tyr Asp Ala Phe Thr Leu Val Arg
1625                 1630                1635

Ala Arg Arg Ala Arg Gly Gln Arg Arg Arg Ala Leu Gly Gln Ala
1640                 1645                1650
```

Ala Gly Thr Gly Phe Gly Ser Pro Ala Ala Pro Phe Pro Glu Pro
         1655                 1660                1665

Pro Pro Ala Phe Ser Pro Gln Ala Pro Ala Ser Thr Ser Arg
         1670                1675                1680

<210> SEQ ID NO 4
<211> LENGTH: 659
<212> TYPE: PRT
<213> ORGANISM: Homo sapiens

<400> SEQUENCE: 4

Gln Ser Glu Glu Ile Gln Gly Arg Glu Lys Ser Arg Pro Asp Leu Gly
1               5                   10                  15

Gly Ala Ser Lys Ala Lys Pro Pro Thr Ala Pro Ala Pro Pro Ser Ala
            20                  25                  30

Pro Ala Pro Ser Ala Gln Pro Thr Pro Pro Ser Ala Ser Val Pro Gly
        35                  40                  45

Lys Lys Ala Arg Glu Glu Ala Pro Gly Pro Pro Gly Val Ser Arg Ala
    50                  55                  60

Asp Met Leu Lys Leu Arg Ser Leu Ser Glu Gly Pro Pro Lys Glu Leu
65                  70                  75                  80

Lys Ile Arg Leu Ile Lys Val Glu Ser Gly Asp Lys Glu Thr Phe Ile
                85                  90                  95

Ala Ser Glu Val Glu Arg Arg Leu Arg Met Ala Asp Leu Thr Ile
            100                 105                 110

Ser His Cys Ala Ala Asp Val Val Arg Ala Ser Arg Asn Ala Lys Val
        115                 120                 125

Lys Gly Lys Phe Arg Glu Ser Tyr Leu Ser Pro Ala Gln Ser Val Lys
    130                 135                 140

Pro Lys Ile Asn Thr Glu Glu Lys Leu Pro Arg Glu Lys Leu Asn Pro
145                 150                 155                 160

Pro Thr Pro Ser Ile Tyr Leu Glu Ser Lys Arg Asp Ala Phe Ser Pro
                165                 170                 175

Val Leu Leu Gln Phe Cys Thr Asp Pro Arg Asn Pro Ile Thr Val Ile
            180                 185                 190

Arg Gly Leu Ala Gly Ser Leu Arg Leu Asn Leu Gly Leu Phe Ser Thr
        195                 200                 205

Lys Thr Leu Val Glu Ala Ser Gly Glu His Thr Val Glu Val Arg Thr
    210                 215                 220

Gln Val Gln Gln Pro Ser Asp Glu Asn Trp Asp Leu Thr Gly Thr Arg
225                 230                 235                 240

Gln Ile Trp Pro Cys Glu Ser Ser Arg Ser His Thr Thr Ile Ala Lys
                245                 250                 255

Tyr Ala Gln Tyr Gln Ala Ser Ser Phe Gln Glu Ser Leu Gln Glu Glu
            260                 265                 270

Lys Glu Ser Glu Asp Glu Glu Ser Glu Glu Pro Asp Ser Thr Thr Gly
        275                 280                 285

Thr Pro Pro Ser Ser Ala Pro Asp Pro Lys Asn His His Ile Ile Lys
    290                 295                 300

Phe Gly Thr Asn Ile Asp Leu Ser Asp Ala Lys Arg Trp Lys Pro Gln
305                 310                 315                 320

Leu Gln Glu Leu Leu Lys Leu Pro Ala Phe Met Arg Val Thr Ser Thr
                325                 330                 335

Gly Asn Met Leu Ser His Val Gly His Thr Ile Leu Gly Met Asn Thr
            340                 345                 350

```
Val Gln Leu Tyr Met Lys Val Pro Gly Ser Arg Thr Pro Gly His Gln
        355                 360                 365

Glu Asn Asn Asn Phe Cys Ser Val Asn Ile Asn Ile Gly Pro Gly Asp
    370                 375                 380

Cys Glu Trp Phe Ala Val His Glu His Tyr Trp Glu Thr Ile Ser Ala
385                 390                 395                 400

Phe Cys Asp Arg His Gly Val Asp Tyr Leu Thr Gly Ser Trp Trp Pro
                405                 410                 415

Ile Leu Asp Asp Leu Tyr Ala Ser Asn Ile Pro Val Tyr Arg Phe Val
                420                 425                 430

Gln Arg Pro Gly Asp Leu Val Trp Ile Asn Ala Gly Thr Val His Trp
                435                 440                 445

Val Gln Ala Thr Gly Trp Cys Asn Asn Ile Ala Trp Asn Val Gly Pro
                450                 455                 460

Leu Thr Ala Tyr Gln Tyr Gln Leu Ala Leu Glu Arg Tyr Glu Trp Asn
465                 470                 475                 480

Glu Val Lys Asn Val Lys Ser Ile Val Pro Met Ile His Val Ser Trp
                485                 490                 495

Asn Val Ala Arg Thr Val Lys Ile Ser Asp Pro Asp Leu Phe Lys Met
                500                 505                 510

Ile Lys Phe Cys Leu Leu Gln Ser Met Lys His Cys Gln Val Gln Arg
                515                 520                 525

Glu Ser Leu Val Arg Ala Gly Lys Lys Ile Ala Tyr Gln Gly Arg Val
                530                 535                 540

Lys Asp Glu Pro Ala Tyr Tyr Cys Asn Glu Cys Asp Val Glu Val Phe
545                 550                 555                 560

Asn Ile Leu Phe Val Thr Ser Glu Asn Gly Ser Arg Asn Thr Tyr Leu
                565                 570                 575

Val His Cys Glu Gly Cys Ala Arg Arg Arg Ser Ala Gly Leu Gln Gly
                580                 585                 590

Val Val Val Leu Glu Gln Tyr Arg Thr Glu Glu Leu Ala Gln Ala Tyr
                595                 600                 605

Asp Ala Phe Thr Leu Val Arg Ala Arg Ala Arg Gly Gln Arg Arg
                610                 615                 620

Arg Ala Leu Gly Gln Ala Ala Gly Thr Gly Phe Gly Ser Pro Ala Ala
625                 630                 635                 640

Pro Phe Pro Glu Pro Pro Ala Phe Ser Pro Gln Ala Pro Ala Ser
                645                 650                 655

Thr Ser Arg

<210> SEQ ID NO 5
<211> LENGTH: 109
<212> TYPE: PRT
<213> ORGANISM: Homo sapiens

<400> SEQUENCE: 5

Gln Leu Tyr Met Lys Val Pro Gly Ser Arg Thr Pro Gly His Gln Glu
1               5                   10                  15

Asn Asn Asn Phe Cys Ser Val Asn Ile Asn Ile Gly Pro Gly Asp Cys
                20                  25                  30

Glu Trp Phe Ala Val His Glu His Tyr Trp Glu Thr Ile Ser Ala Phe
            35                  40                  45

Cys Asp Arg His Gly Val Asp Tyr Leu Thr Gly Ser Trp Trp Pro Ile
        50                  55                  60
```

Leu Asp Asp Leu Tyr Ala Ser Asn Ile Pro Val Tyr Arg Phe Val Gln
65                  70                  75                  80

Arg Pro Gly Asp Leu Val Trp Ile Asn Ala Gly Thr Val His Trp Val
            85                  90                  95

Gln Ala Thr Gly Trp Cys Asn Asn Ile Ala Trp Asn Val
            100                 105

<210> SEQ ID NO 6
<211> LENGTH: 2541
<212> TYPE: DNA
<213> ORGANISM: Homo sapiens

<400> SEQUENCE: 6

| | | | | | |
|---|---|---|---|---|---|
| gggttggacc | ctcgtacaga | agctaatacg | actcactata | gggaaataag | agagaaaaga | 60 |
| agagtaagaa | gaaatataag | agccaccccg | cggtggcggc | cgctctagaa | ctagtggatc | 120 |
| ccccgggctg | caggaattcg | ataaaagcga | tcgcccatca | caagtttgta | caaaaaagca | 180 |
| ggcttagcca | ccatgtaccc | atacgatgtt | ccagattacg | ctcctaagaa | aaagaggaag | 240 |
| gtgcagagcg | aggagatcca | gggtcgtgag | aagtcccggc | ccgatcttgg | cggggcctcc | 300 |
| aaggccaagc | cacccacagc | tccagcccct | ccatcagctc | ctgcaccttc | tgcccagccc | 360 |
| acaccccgt | cagcctctgt | ccctggaaag | aaggctcggg | aggaagcccc | agggccaccg | 420 |
| ggtgtcagcc | gggccgacat | gctgaagctg | cgctcactta | gtgaggggcc | ccccaaggag | 480 |
| ctgaagatcc | ggctcatcaa | ggtagagagt | ggtgacaagg | agacctttat | cgcctctgag | 540 |
| gtggaagagc | ggcggctgcg | catggcagac | ctcaccatca | gccactgtgc | tgctgacgtc | 600 |
| gtgcgcgcca | gcaggaatgc | caaggtgaaa | gggaagtttc | gagagtccta | cctttcccct | 660 |
| gcccagtctg | tgaaaccgaa | gatcaacact | gaggagaagc | tgccccggga | aaaactcaac | 720 |
| ccccctacac | ccagcatcta | tctggagagc | aaacgggatg | ccttctcacc | tgtcctgctg | 780 |
| cagttctgta | cagaccctcg | aaatcccatc | acagtgatcc | ggggcctggc | gggctccctg | 840 |
| cggctcaact | tgggcctctt | ctccaccaag | accctggtgg | aagcgagtgg | cgaacacacc | 900 |
| gtggaagttc | gcacccaggt | gcagcagccc | tcagatgaga | ctgggatct | gacaggcact | 960 |
| cggcagatct | ggccttgtga | gagctcccgt | tcccacacca | ccattgccaa | gtacgcacag | 1020 |
| taccaggcct | catccttcca | ggagtctctg | caggaggaga | aggagagtga | ggatgaggag | 1080 |
| tcagaggagc | cagacagcac | cactggaacc | cctcctagca | gcgcaccaga | cccgaagaac | 1140 |
| catcacatca | tcaagtttgg | caccaacatc | gacttgtctg | atgctaagcg | gtggaagccc | 1200 |
| cagctgcagg | agctgctgaa | gctgcccgcc | ttcatgcggg | taacatccac | gggcaacatg | 1260 |
| ctgagccacg | tgggccacac | catcctgggc | atgaacacgg | tgcagctgta | catgaaggtg | 1320 |
| cccggcagcc | gaacgccagg | ccaccaggag | aataacaact | tctgctccgt | caacatcaac | 1380 |
| attgcccag | cgactgcga | gtggttcgcg | gtgcacgagc | actactggga | gaccatcagc | 1440 |
| gctttctgtg | atcggcacgg | cgtggactac | ttgacgggtt | cctggtggcc | aatcctggat | 1500 |
| gatctctatg | catccaatat | tcctgtgtac | cgcttcgtgc | agcgacccgg | agacctcgtg | 1560 |
| tggattaatg | cggggactgt | gcactgggtg | caggccaccg | gctggtgcaa | caacattgcc | 1620 |
| tggaacgtgg | ggcccctcac | cgcctatcag | taccagctgg | ccctggaacg | atacgagtgg | 1680 |
| aatgaggtga | gaacgtcaa | atccatcgtg | cccatgattc | acgtgtcatg | gacgtggct | 1740 |
| cgcacggtca | aaatcagcga | ccccgacttg | ttcaagatga | tcaagttctg | cctgctgcag | 1800 |
| tccatgaagc | actgccaggt | gcaacgcgag | agcctggtgc | gggcagggaa | gaaaatcgct | 1860 |

```
taccagggcc gtgtcaagga cgagccagcc tactactgca acgagtgcga tgtggaggtg    1920
tttaacatcc tgttcgtgac aagtgagaat ggcagccgca acacgtacct ggtacactgc    1980
gagggctgtg cccggcgccg cagcgcaggc ctgcagggcg tggtggtgct ggagcagtac    2040
cgcactgagg agctggctca ggcctacgac gccttcacgc tggtgagggc ccggcgggcg    2100
cgcgggcagc ggaggagggc actggggcag gctgcaggga cgggcttcgg gagcccggcc    2160 gcgccttttcc ctgagccccc gccggctttc tccccccagg ccccagccag cacgtcgcga    2220
tgaacccagc tttcttgtac aaagtggtga tggccgctgt ttaaaacttt tatcaagctt    2280
atcgataccg tcgacctcga atgctgcctt ctgcggggct tgccttctgg ccatgccctt    2340
cttctctccc ttgcacctgt acctcttggt ctttgaataa agcctgagta ggaagtgagg    2400
gtctagaact agtgtcgacg caaaaaaaaa aaaaaaaaaa aaaaaaaaaa aaaaaaaaaa    2460
aaaaaaaaaa aaaaaaaaaa aaaaaaaaaa aaaaaaaaaa aaaaaaaaaa aaaaaaaaaa    2520
aaaaaaaaaa aaaaaaaaaa a                                              2541

<210> SEQ ID NO 7
<211> LENGTH: 1574
<212> TYPE: DNA
<213> ORGANISM: Homo sapiens

<400> SEQUENCE: 7
gggttggacc ctcgtacaga agctaatacg actcactata gggaaataag agagaaaaga      60
agagtaagaa gaaatataag agccaccccg cggtggcggc cgctctagaa ctagtggatc     120
ccccgggctg caggaattcg ataaaagcga tcgcccatca caagtttgta caaaaaagca     180
ggctccgcgg ccgcccccctt caccgctagg gataacaggg taatagaagg agccgccacc    240
atggagctac tgtcgccacc gctccgcgac gtagacctga cggccccccga cggctctctc    300 tgctcctttg ccacaacgga cgacttctat gacgacccgt gtttcgactc cccggacctg    360
cgcttcttcg aagacctgga cccgcgcctg atgcacgtgg gcgcgctcct gaaacccgaa    420
gagcactcgc acttccccgc ggcggtgcac ccggccccgg gcgcacgtga ggacgagcat    480
gtgcgcgcgc ccagcgggca ccaccaggcg ggccgctgcc tactgtgggc ctgcaaggcg    540
tgcaagcgca agaccaccaa cgccgaccgc cgcaaggccg ccaccatgcg cgagcggcgc    600
cgcctgagca aagtaaatga ggcctttgag acactcaagc gctgcacgtc gagcaatcca    660
aaccagcggt tgcccaaggt ggagatcctg cgcaacgcca tccgctatat cgagggcctg    720
caggctctgc tgcgcgacca ggacgccgcg ccccctggcg ccgcagccgc cttctatgcg    780
ccgggcccgc tgccccccggg ccgcggcggc gagcactaca gcggcgactc cgacgcgtcc    840
agcccgcgct ccaactgctc cgacggcatg atggactaca gcggccccc gagcggcgcc    900 cggcggcgga actgctacga aggcgcctac tacaacgagg cgcccagcga acccaggccc    960
gggaagagtg cggcggtgtc gagcctagac tgcctgtcca gcatcgtgga gcgcatctcc    1020
accgagagcc ctgcggcgcc cgccctcctg ctggcggacg tgccttctga gtcgcctccg    1080
cgcaggcaag aggctgccgc ccccagcgag ggagagagca gcgcgaccc cacccagtca    1140 ccggacgccc cccgcagtg ccctgcgggt gcgaaccca acccgatata ccaggtgctc    1200
tgagtttcct gtgaacaatt gctcctctct taaggtagca aagggtgggc gcgccgaccc    1260
agctttcttg tacaaagtgg tgatggccgc tgtttaaaac ttttatcaag cttatcgata    1320
ccgtcgacct cgaatgctgc cttctgcggg gcttgccttc tggccatgcc cttcttctct    1380
```

```
ccccttgcacc tgtacctctt ggtctttgaa taaagcctga gtaggaagtg agggtctaga    1440
actagtgtcg acgcaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaa                                                       1574
```

<210> SEQ ID NO 8
<211> LENGTH: 320
<212> TYPE: PRT
<213> ORGANISM: Homo sapiens

<400> SEQUENCE: 8

```
Met Glu Leu Leu Ser Pro Pro Leu Arg Asp Val Asp Leu Thr Ala Pro
 1               5                  10                  15

Asp Gly Ser Leu Cys Ser Phe Ala Thr Thr Asp Asp Phe Tyr Asp Asp
            20                  25                  30

Pro Cys Phe Asp Ser Pro Asp Leu Arg Phe Phe Glu Asp Leu Asp Pro
        35                  40                  45

Arg Leu Met His Val Gly Ala Leu Leu Lys Pro Glu Glu His Ser His
    50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
    130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Ala Phe Tyr Ala Pro Gly Pro Leu Pro Pro Gly Arg Gly Gly Glu His
            180                 185                 190

Tyr Ser Gly Asp Ser Asp Ala Ser Ser Pro Arg Ser Asn Cys Ser Asp
        195                 200                 205

Gly Met Met Asp Tyr Ser Gly Pro Pro Ser Gly Ala Arg Arg Arg Asn
    210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
                245                 250                 255

Glu Arg Ile Ser Thr Glu Ser Pro Ala Ala Pro Ala Leu Leu Leu Ala
            260                 265                 270

Asp Val Pro Ser Glu Ser Pro Pro Arg Arg Gln Glu Ala Ala Ala Pro
        275                 280                 285

Ser Glu Gly Glu Ser Ser Gly Asp Pro Thr Gln Ser Pro Asp Ala Ala
    290                 295                 300

Pro Gln Cys Pro Ala Gly Ala Asn Pro Asn Pro Ile Tyr Gln Val Leu
305                 310                 315                 320
```

<210> SEQ ID NO 9
<211> LENGTH: 1153

<212> TYPE: DNA
<213> ORGANISM: Homo sapiens

<400> SEQUENCE: 9

```
gggttggacc ctcgtacaga agctaatacg actcactata gggaaataag agagaaaaga      60
agagtaagaa gaaatataag agccaccccg cggtggcggc cgctctagaa ctagtggatc     120
ccccgggctg caggaattcg ataaaagcga tcgcccatca caagtttgta caaaaaagca     180
ggcttcacca tgacgcctca accctcgggt gcgcccactg tccaagtgac ccgtgagacg     240
gagcggtcct tccccagagc ctcggaagac gaagtgacct gccccacgtc cgccccgccc     300
agccccactc gcacacgggg gaactgcgca gaggcggaag agggaggctg ccgaggggcc     360
ccgaggaagc tccgggcacg gcgcggggga cgcagccggc ctaagagcga gttggcactg     420
agcaagcagc gacggagtcg gcgaaagaag gccaacgacc gcgagcgcaa tcgaatgcac     480
aacctcaact cggcactgga cgccctgcgc ggtgtcctgc ccaccttccc agacgacgcg     540
aagctcacca agatcgagac gctgcgcttc gcccacaact acatctgggc gctgactcaa     600
acgctgcgca tagcggacca cagcttgtac gcgctggagc cgccggcgcc gcactgcggg     660
gagctgggca gccaggcgg ttccccgggg gactgggggt ccctctactc cccagtctcc     720
caggctggca gcctgagtcc cgccgcgtcg ctggaggagc gacccgggct gctggggggcc     780
acctttccg cctgcttgag cccaggcagt ctggctttct cagattttct gtgagaccca     840
gctttcttgt acaaagtggt gatggccgct gtttaaaact tttatcaagc ttatcgatac     900
cgtcgacctc gaatgctgcc ttctgcgggg cttgccttct ggccatgccc ttcttctctc     960
ccttgcacct gtacctcttg gtctttgaat aaagcctgag taggaagtga gggtctagaa    1020
ctagtgtcga cgcaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaa                                                        1153
```

<210> SEQ ID NO 10
<211> LENGTH: 214
<212> TYPE: PRT
<213> ORGANISM: Homo sapiens

<400> SEQUENCE: 10

```
Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140
```

```
Ser Leu Tyr Ala Leu Glu Pro Pro Ala Pro His Cys Gly Glu Leu Gly
145                 150                 155                 160
Ser Pro Gly Gly Ser Pro Gly Asp Trp Gly Ser Leu Tyr Ser Pro Val
                165                 170                 175
Ser Gln Ala Gly Ser Leu Ser Pro Ala Ala Ser Leu Glu Glu Arg Pro
            180                 185                 190
Gly Leu Leu Gly Ala Thr Phe Ser Ala Cys Leu Ser Pro Gly Ser Leu
        195                 200                 205
Ala Phe Ser Asp Phe Leu
    210

<210> SEQ ID NO 11
<211> LENGTH: 2414
<212> TYPE: DNA
<213> ORGANISM: Homo sapiens

<400> SEQUENCE: 11
```

| | | | | |
|---|---|---|---|---|
| gggttggacc ctcgtacaga agctaatacg actcactata gggaaataag agagaaaaga | 60 |
| agagtaagaa gaaatataag agccaccccg cggtggcggc cgctctagaa ctagtggatc | 120 |
| cccgggctg caggaattcg ataaaagcga tcgcccatca caagtttgta caaaaaagca | 180 |
| ggctccacca tggtttctaa actgagccag ctgcagacgg agctcctggc ggccctgctg | 240 |
| gagtcagggc tgagcaaaga ggcactgctc caggcactgg gtgagccggg ccctacctc | 300 |
| ctggctggag aaggccccct ggacaagggg gagtcctgcg gcggcggtcg aggggagctg | 360 |
| gctgagctgc ccaatgggct gggggagact cggggctccg aggacgagac ggacgacgat | 420 |
| ggggaagact tcacgccacc catcctcaaa gagctggaga acctcagccc tgaggaggcg | 480 |
| gcccaccaga aagccgtggt ggagaccctt ctgcaggagg acccgtggcg tgtggcgaag | 540 |
| atggtcaagt cctacctgca gcagcacaac atcccacagc gggaggtggt cgataccact | 600 |
| ggcctcaacc agtcccacct gtcccaacac ctcaacaagg gcactcccat gaagacgcag | 660 |
| aagcgggccg ccctgtacac ctggtacgtc cgcaagcagc gagaggtggc gcagcagttc | 720 |
| acccatgcag gcagggagg gctgattgaa gagcccacag gtgatgagct accaaccaag | 780 |
| aaggggcgga ggaaccgttt caagtggggc ccagcatccc agcagatcct gttccaggcc | 840 |
| tatgagaggc agaagaaccc tagcaaggag gagcgagaga cgctagtgga ggagtgcaat | 900 |
| agggcggaat gcatccagag aggggtgtcc ccatcacagg cacaggggct gggctccaac | 960 |
| ctcgtcacgg aggtgcgtgt ctacaactgg tttgccaacc ggcgcaaaga agaagccttc | 1020 |
| cggcacaagc tggccatgga cgtacagc gggcccccc cagggccagg cccgggacct | 1080 |
| gcgctgcccg ctcacagctc ccctggcctg cctccacctg cctctcccc cagtaaggtc | 1140 |
| cacggtgtgc gctatggaca gcctgcgacc agtgagactg cagaagtacc ctcaagcagc | 1200 |
| ggcggtccct tagtgacagt gtctacaccc ctccaccaag tgtccccac gggcctggag | 1260 |
| cccagccaca gcctgctgag tacagaagcc aagctggtct cagcagctgg ggccccctc | 1320 |
| cccctgtca gcaccctgac agcactgcac agcttggagc agacatcccc aggcctcaac | 1380 |
| cagcagcccc agaacctcat catggcctca cttcctgggg tcatgaccat cgggcctggt | 1440 |
| gagcctgcct ccctgggtcc tacgttcacc aacacaggtg cctccaccct ggtcatcggc | 1500 |
| ctggcctcca cgcaggcaca gagtgtgccc gtcatcaaca gcatgggcag cagcctgacc | 1560 |
| accctgcagc ccgtccagtt ctcccagccg ctgcacccct cctaccagca gccgctcatg | 1620 |
| ccacctgtgc agagccatgt gacccagagc ccttcatgg ccaccatggc tcagctgcag | 1680 |

-continued

```
agcccccacg ccctctacag ccacaagccc gaggtggccc agtacaccca cacaggcctg    1740
ctcccgcaga ctatgctcat caccgacacc accaacctga gcgccctggc cagcctcacg    1800
cccaccaagc aggtcttcac ctcagacact gaggcctcca gtgagtccgg gcttcacacg    1860
ccggcatctc aggccaccac cctccacgtc cccagccagg accctgccgg catccagcac    1920
ctgcagccgg ccaccggct cagcgccagc ccacagtgt cctccagcag cctggtgctg    1980
taccagagct cagactccag caatggccag agccacctgc tgccatccaa ccacagcgtc    2040
atcgagacct tcatctccac ccagatggcc tcttcctccc agttgtgagc ggccgcaccc    2100
agctttcttg tacaaagtgg tgatggccgc tgtttaaaac ttttatcaag cttatcgata    2160
ccgtcgacct cgaatgctgc cttctgcggg gcttgccttc tggccatgcc cttcttctct    2220
cccttgcacc tgtacctctt ggtctttgaa taaagcctga gtaggaagtg agggtctaga    2280
actagtgtcg acgcaaaaaa aaaaaaaaaa aaaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaaaaaa aaaa                                                      2414
```

<210> SEQ ID NO 12
<211> LENGTH: 632
<212> TYPE: PRT
<213> ORGANISM: Homo sapiens

<400> SEQUENCE: 12

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Leu Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240
```

-continued

```
Cys Ile Gln Arg Gly Val Ser Pro Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
    370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Phe Thr
    530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
        595                 600                 605

His Leu Leu Pro Ser Asn His Ser Val Ile Glu Thr Phe Ile Ser Thr
    610                 615                 620

Gln Met Ala Ser Ser Ser Gln Leu
625                 630

<210> SEQ ID NO 13
<211> LENGTH: 12
```

```
<212> TYPE: PRT
<213> ORGANISM: Human immunodeficiency virus

<400> SEQUENCE: 13

Gly Arg Lys Lys Arg Arg Gln Arg Arg Pro Gln
1               5                   10

<210> SEQ ID NO 14
<211> LENGTH: 8
<212> TYPE: PRT
<213> ORGANISM: Artificial Sequence
<220> FEATURE:
<223> OTHER INFORMATION: r8

<400> SEQUENCE: 14

Arg Arg Arg Arg Arg Arg Arg Arg
1               5

<210> SEQ ID NO 15
<211> LENGTH: 21
<212> TYPE: PRT
<213> ORGANISM: Artificial Sequence
<220> FEATURE:
<223> OTHER INFORMATION: MPG-8
<220> FEATURE:
<221> NAME/KEY: MISC_FEATURE
<222> LOCATION: (1)..(1)
<223> OTHER INFORMATION: Xaa stands for bAla.

<400> SEQUENCE: 15

Xaa Phe Leu Gly Trp Leu Gly Ala Trp Gly Thr Met Gly Trp Ser Pro
1               5                   10                  15

Lys Lys Lys Arg Lys
            20

<210> SEQ ID NO 16
<211> LENGTH: 21
<212> TYPE: DNA
<213> ORGANISM: Artificial Sequence
<220> FEATURE:
<223> OTHER INFORMATION: siPOU5F1 sense strand
<220> FEATURE:
<221> NAME/KEY: misc_RNA
<222> LOCATION: (1)..(21)
<223> OTHER INFORMATION: Combined DNA/RNA molecule. RNA bases are from 1
      to 19. DNA bases are from 20 to 21.
<220> FEATURE:
<221> NAME/KEY: misc_difference
<222> LOCATION: (20)..(21)
<223> OTHER INFORMATION: 30 spermines are added between thymines.

<400> SEQUENCE: 16
gcccgaaaga gaaagcgaat t                                          21

<210> SEQ ID NO 17
<211> LENGTH: 21
<212> TYPE: DNA
<213> ORGANISM: Artificial Sequence
<220> FEATURE:
<223> OTHER INFORMATION: siPOU5F1 anti-sense strand
<220> FEATURE:
<221> NAME/KEY: misc_RNA
<222> LOCATION: (1)..(21)
<223> OTHER INFORMATION: Combined DNA/RNA molecule. RNA bases are from 1
      to 19. DNA bases are from 20 to 21.

<400> SEQUENCE: 17
uucgcuuucu cuuucgggcc t                                          21
```

<210> SEQ ID NO 18
<211> LENGTH: 816
<212> TYPE: DNA
<213> ORGANISM: Homo sapiens

<400> SEQUENCE: 18

| | | | | | |
|---|---|---|---|---|---|
| atgttacagg | cgtgcaaaat | ggaagggttt | cccctcgtcc | cccctcagcc | atcagaagac | 60 |
| ctggtgccct | atgacacgga | tctataccaa | cgccaaacgc | acgagtatta | ccctatctc | 120 |
| agcagtgatg | gggagagcca | tagcgaccat | tactgggact | tccaccccca | ccacgtgcac | 180 |
| agcgagttcg | agagcttcgc | cgagaacaac | ttcacggagc | tccagagcgt | gcagccccg | 240 |
| cagctgcagc | agctctaccg | ccacatggag | ctggagcaga | tgcacgtcct | cgataccccc | 300 |
| atggtgccac | cccatcccag | tcttggccac | caggtctcct | acctgccccg | gatgtgcctc | 360 |
| cagtacccat | ccctgtcccc | agcccagccc | agctcagatg | aggaggaggg | cgagcggcag | 420 |
| agccccccac | tggaggtgtc | tgacggcgag | gcggatggcc | tggagcccgg | gcctgggctc | 480 |
| ctgcctgggg | agacaggcag | caagaagaag | atccgcctgt | accagttcct | gttggacctg | 540 |
| ctccgcagcg | gcgacatgaa | ggacagcatc | tggtgggtgg | acaaggacaa | gggcaccttc | 600 |
| cagttctcgt | ccaagcacaa | ggaggcgctg | gcgcaccgct | gggcatcca | aagggcaac | 660 |
| cgcaagaaga | tgacctacca | gaagatggcg | cgcgcgctgc | gcaactacgg | caagacgggc | 720 |
| gaggtcaaga | aggtgaagaa | gaagctcacc | taccagttca | gcggcgaagt | gctgggccgc | 780 |
| gggggcctgg | ccgagcggcg | ccacccgccc | cactga | | | 816 |

<210> SEQ ID NO 19
<211> LENGTH: 271
<212> TYPE: PRT
<213> ORGANISM: Homo sapiens

<400> SEQUENCE: 19

Met Leu Gln Ala Cys Lys Met Glu Gly Phe Pro Leu Val Pro Pro Gln
1               5                   10                  15

Pro Ser Glu Asp Leu Val Pro Tyr Asp Thr Asp Leu Tyr Gln Arg Gln
            20                  25                  30

Thr His Glu Tyr Tyr Pro Tyr Leu Ser Ser Asp Gly Glu Ser His Ser
        35                  40                  45

Asp His Tyr Trp Asp Phe His Pro His His Val His Ser Glu Phe Glu
    50                  55                  60

Ser Phe Ala Glu Asn Asn Phe Thr Glu Leu Gln Ser Val Gln Pro Pro
65                  70                  75                  80

Gln Leu Gln Gln Leu Tyr Arg His Met Glu Leu Glu Gln Met His Val
                85                  90                  95

Leu Asp Thr Pro Met Val Pro Pro His Pro Ser Leu Gly His Gln Val
            100                 105                 110

Ser Tyr Leu Pro Arg Met Cys Leu Gln Tyr Pro Ser Leu Ser Pro Ala
        115                 120                 125

Gln Pro Ser Ser Asp Glu Glu Glu Gly Glu Arg Gln Ser Pro Pro Leu
    130                 135                 140

Glu Val Ser Asp Gly Glu Ala Asp Gly Leu Glu Pro Gly Pro Gly Leu
145                 150                 155                 160

Leu Pro Gly Glu Thr Gly Ser Lys Lys Lys Ile Arg Leu Tyr Gln Phe
                165                 170                 175

Leu Leu Asp Leu Leu Arg Ser Gly Asp Met Lys Asp Ser Ile Trp Trp
            180                 185                 190

-continued

```
Val Asp Lys Asp Lys Gly Thr Phe Gln Phe Ser Ser Lys His Lys Glu
        195                 200                 205

Ala Leu Ala His Arg Trp Gly Ile Gln Lys Gly Asn Arg Lys Lys Met
        210                 215                 220

Thr Tyr Gln Lys Met Ala Arg Ala Leu Arg Asn Tyr Gly Lys Thr Gly
225                 230                 235                 240

Glu Val Lys Lys Val Lys Lys Lys Leu Thr Tyr Gln Phe Ser Gly Glu
                245                 250                 255

Val Leu Gly Arg Gly Gly Leu Ala Glu Arg Arg His Pro Pro His
                260                 265                 270
```

COMPOSITIONS AND METHODS FOR DIFFERENTIATION OF HUMAN PLURIPOTENT STEM CELLS INTO DESIRED CELL TYPES

1. FIELD OF THE INVENTION

The present application is a divisional application of U.S. patent application Ser. No. 15/905,982 filed Feb. 27, 2018 which claims priority from US Provisional Patent Application No. 62/465,188 and U.S. Provisional Patent Application No. 62/523,324, which are incorporated herein by reference. The present invention relates to a method of efficiently differentiating a pluripotent stem cell into a desired cell type.

2. DESCRIPTION OF THE RELATED ART

Human pluripotent stem cells (hPSCs), such as human embryonic stem cells (hESCs) and human induced pluripotent stem cells (hiPSCs), have potentials to become all cell types in a human body in vitro. For the last 20 years, use of neurons, muscles, and other cell types differentiated from hPSCs for cell transplantation therapy and drug screening has been widely investigated, and practical application thereof has been under consideration. However, the practical application is limited, and one of the major obstacles is difficulty of differentiating hPSCs into desired cell types, such as neurons and muscles.

The most generally used method is step-by-step differentiation based on successive changes in cell culture environment (Hu et al., 2010, PNAS 107, 4335-4340). Those differentiation steps have been well established and widely used, but have fundamental limitations in both speed and scale. Further, the process is relatively slow, and takes several weeks until formation of functional neurons as the desired cell type.

As another method, PSCs can be rapidly and efficiently differentiated by inducing or overexpressing transcription factors (TFs) with plasmids, viruses, and other vectors (Busskamp et al., 2014, Molecular Systems Biology 10, 760; Hester et al., Molecular Therapy, 19, 1905-1912; Zhang et al., 2013, Neuron, 78, 785-798).

The inventors of the present invention have reported rapid and efficient differentiation into skeletal muscles (Akiyama et al., 2016, Development 143, 3674), motor neurons (Goparaju et al., 2017, Scientific Reports 7, 42367), and lacrimal gland epithelium-like cells (Hirayama et al., npj Aging and Mechanisms of Disease 2017, 1) by transfection of a cocktail of synthetic mRNAs encoding TFs into hPSCs. The differentiation method based on synthetic mRNA has many desirable features. mRNA is not incorporated into a cellular genome, and hence achieves safe and footprint-free transfer of a gene product. However, this method requires a plurality of times of transfection of synthetic mRNAs into cells, typically one or two times of transfection a day for several consecutive days. Thus, this method puts a huge burden on an experimenter, and requires expert skills.

In related-art methods of differentiating pluripotent stem cells into a desired cell type, there has not been established a differentiation induction method using human ES/iPS cells and being stable and highly efficient. Many attempts have been made, which includes a step-by-step differentiation induction method based on the control of culture conditions or the addition of, for example, various cell growth factors/differentiation factors to a culture solution, but the use of complicated culture steps is a big problem. In addition, there are also big problems in, for example, that the speed of cell differentiation is low, and hence long-period culture is required, and that the differentiation efficiency is low, and hence it is difficult to obtain a sufficient number of required cells.

SUMMARY OF THE INVENTION

The inventors of the present invention have developed a method of inducing differentiation into a desired cell type within a short period of time and with high efficiency by the use of a Sendai virus vector capable of expressing a transcription factor, and as required, the use of a pluripotent stem cell in which an expression amount of a POU5F1 protein has been substantially removed or reduced.

Thus, the present invention has been completed.

That is, the present invention includes the following.

1. A method of differentiating a pluripotent stem cell into a desired cell type, including:
    1) adding a Sendai virus vector containing a transcription factor required for induction of differentiation into the desired cell type to a pluripotent stem cell in a cell culture medium; and
    2) culturing the pluripotent stem cell to differentiate the pluripotent stem cell into the desired cell type.
2. A method according to the above-mentioned item 1, further including adding a gene for a compound having an action of substantially removing or reducing an expression amount of a POU5F1 protein to the pluripotent stem cell.
3. A method according to the above-mentioned item 2, wherein the gene for the compound having an action of substantially removing or reducing an expression amount of a POU5F1 protein includes siRNA against POU5F1.
4. A method according to the above-mentioned item 1, in which the pluripotent stem cell includes a pluripotent stem cell in which an expression amount of a POU5F1 protein has been substantially removed or reduced.
5. A method according to any one of the above-mentioned items 1 to 4, wherein the adding a Sendai virus vector containing a transcription factor required for induction of differentiation into the desired cell type is performed once.
6. A method according to any one of the above-mentioned items 1 to 5, wherein the Sendai virus vector is temperature-sensitive.
7. A method according to any one of the above-mentioned items 1 to 6, wherein the desired cell type includes a skeletal muscle cell, and wherein the transcription factor includes MYOD1.
8. A method according to the above-mentioned item 7, wherein differentiation efficiency of the skeletal muscle cell is 75% or more.
9. A method according to the above-mentioned item 7 or 8, wherein differentiation efficiency of the skeletal muscle cell is 75% or more, and wherein one kind of cell culture medium is used.
10. A method according to any one of the above-mentioned items 1 to 6, wherein the desired cell type includes a motor neuron, and wherein the transcription factor includes NEUROG3.
11. A method according to the above-mentioned item 10, wherein differentiation efficiency of the motor neuron is about 90%.

12. A method according to the above-mentioned item 10 or 11, wherein differentiation efficiency of the motor neuron is about 90%, and wherein one kind of cell culture medium is used.
13. A method according to any one of the above-mentioned items 1 to 6, wherein the desired cell type includes a liver cell, and wherein the transcription factor includes FOXA1 and HNF1A.
14. A method according to the above-mentioned item 13, wherein two kinds of cell culture media are used.
15. A method according to any one of the above-mentioned items 1 to 6, wherein the desired cell type includes a hematopoietic cell, and wherein the transcription factor includes SPI1.
16. A method according to any one of the above-mentioned items 1 to 6, wherein the desired cell type includes a dopaminergic neuron, and wherein the transcription factor includes FOXA1.

The method of efficiently differentiating a pluripotent stem cell into a desired cell type of the present invention has at least any one or more of the following effects.

(1) The period of time required for cell differentiation starting with the pluripotent stem cell is shortened and the differentiation induction efficiency is improved.
(2) Differentiation can be performed by adding the transcription factor required for induction of differentiation into the desired cell type only once.
(3) The number of kinds of transcription factors required for induction of differentiation into the desired cell type can be decreased as compared to related-art methods.
(4) When the method is combined with a method of reducing the undifferentiation maintenance of a pluripotent stem cell and/or a method of reducing the differentiation resistance thereof, the period of time required for cell differentiation starting with the pluripotent stem cell is shortened and the differentiation induction efficiency is improved.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

FIG. 1A is a schematic of typical experimental steps. On Day 1, human iPS cells were plated on a cell culture dish. Immediately after the plating, a Sendai virus vector encoding a human MYOD1 gene was added to the cell culture medium. The cells were cultured in a $CO_2$ incubator at 33° C. On Day 2, siPOU5F1 was added to the cell culture medium. On Day 4, the temperature of the $CO_2$ incubator was changed to 37° C. On Day 6, in order to evaluate the efficiency of cell differentiation, the cells were fixed, and used for immunostaining. FIG. 1B is a microscopic image (10× objective lens) of cells immunostained with anti-myosin heavy chain (red signal), which is specific for mature skeletal muscles. The cells were further stained with DAPI (green signal) for visualizing the nuclei of all cells. FIG. 1C is a microscopic image (20× objective lens) of cells immunostained with anti-myosin heavy chain (red signal), which is specific for mature skeletal muscles. The cells were further stained with DAPI (green signal) for visualizing the nuclei of all cells.

FIG. 2A, FIG. 2B, FIG. 2C, FIG. 2D, and FIG. 2E are a schematic and images for illustrating and showing differentiation into cholinergic and/or motor neurons. FIG. 2A is a schematic of typical experimental steps. On Day 1, human iPS cells were plated on a cell culture dish. Immediately after the plating, a Sendai virus vector encoding a human NGN3 gene was added to the cell culture medium. The cells were cultured in a $CO_2$ incubator at 33° C. On Day 3, the temperature of the $CO_2$ incubator was changed to 37° C. On Day 4, the cells were re-plated on a glass coverslip. On Day 6, in order to evaluate the efficiency of cell differentiation, the cells were fixed, and used for immunostaining. FIG. 2B is a microscopic image (20× objective lens) of cells stained with DAPI (blue signal) for visualizing the nuclei of all cells. FIG. 2C is a microscopic image (20× objective lens) of cells immunostained with anti-β3-tubulin (TUBB3) (red signal), which is specific for mature neurons. FIG. 2D is a microscopic image (20× objective lens) of cells immunostained with anti-choline acetyltransferase (ChAT) antibody (green signal), which is specific for mature motor neurons. FIG. 2E is a synthetic image of FIG. 2C and FIG. 2D.

FIG. 3A is a schematic of typical experimental steps. On Day 1, human iPS cells were plated on a cell culture dish. Immediately after the plating, a mixture of equal amounts of a Sendai virus vector encoding a human FOXA1 gene and a Sendai virus vector encoding a human HNF1A gene was added to the cell culture medium. The cell culture medium is a ROCK-inhibitor (Y27632)-containing StemFit (registered trademark in Japan) Basic02 (Ajinomoto). The cells were cultured in a $CO_2$ incubator at 33° C. On Day 2, siPOU5F1 was added to the cell culture medium. The cell culture medium was replaced with a differentiation medium. On Day 5, the temperature of the $CO_2$ incubator was changed to 37° C. On Day 7, the cell culture medium was replaced with a maturation medium. On Day 8, in order to evaluate the efficiency of cell differentiation, the cells were fixed, and used for immunostaining. FIG. 3B is a microscopic image (10× objective lens) of cells immunostained with anti-α-fetoprotein (AFP) antibody (red signal), which is a fetal form of albumin and is specific for embryonic liver cells. FIG. 3C is a microscopic image (10× objective lens) of cells immunostained with anti-albumin (ALB) antibody (green signal), which is specific for liver cells. FIG. 3D is a microscopic image (20× objective lens) of cells immunostained with anti-α-fetoprotein (AFP) antibody (red signal), which is a fetal form of albumin and is specific for embryonic liver cells. FIG. 3E is a microscopic image (20× objective lens) of cells immunostained with anti-albumin (ALB) antibody (green signal), which is specific for liver cells.

DESCRIPTION OF THE EMBODIMENTS

The Present Invention

Figure 1A:
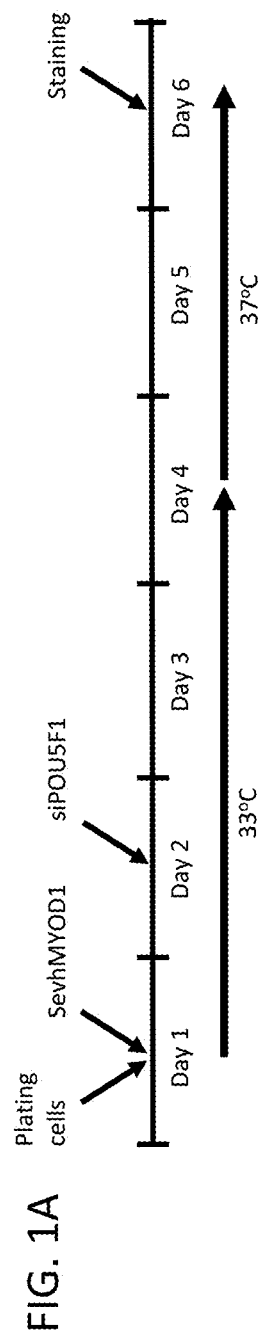
FIG. 1A, FIG. 1B, and FIG. 1C are a schematic and images for illustrating and showing differentiation into skeletal muscles.

A method of efficiently differentiating a pluripotent stem cell into a desired cell type of the present invention (hereinafter sometimes referred to as "method of the present invention") includes part or all of the following steps, though the method is not particularly limited as long as the method uses a Sendai virus vector capable of expressing a transcription factor required for induction of differentiation into the desired cell type:

1) a step of adding a Sendai virus vector containing a transcription factor required for induction of differentiation into the desired cell type to a pluripotent stem cell in a cell culture medium; and 2) a step of culturing the pluripotent stem cell to differentiate the pluripotent stem cell into the desired cell type.

The adding of various compounds, transcription factors, vectors and the like to the pluripotent stem cell encompasses addition to a medium in which the pluripotent stem cell is present.

(Pluripotent Stem Cell)

The pluripotent stem cell to be used in the method of the present invention is not particularly limited, but is preferably derived from a mammal, particularly preferably derived from a human. The pluripotent stem cell is, for example, a human ES cell, a human iPS cell, or any combination thereof, is not particularly limited, and encompasses tissue stem cells derived from tissues and organs, dermal fibroblasts, and all kinds of cells derived from tissues and organs.

(Sendai Virus Vector)

Sendai virus is a kind of virus of the genus Respirovirus of the family Paramyxoviridae, and has single-stranded RNA as its genes.

The Sendai virus vector to be used in the method of the present invention may be a natural strain, a wild-type strain, a mutant strain, or a commercially available product (e.g., from ID Pharma).

An example thereof may be an F gene-deleted Sendai virus vector having G69E, T116A, and A183S mutations in M protein, A262T, G264R, and K461G mutations in HN protein, D433A, R434A, K437A, and L511F mutations in P protein, and L1361C, L1558I, N1197S, and K1795E mutations in L protein.

In addition, the Sendai virus vector to be used in the method of the present invention is preferably a temperature-sensitive strain. The term "temperature-sensitive" refers to a significant lowering of activity at a general cell culture temperature (e.g., from 37° C. to 38° C.) as compared to low temperature (e.g., from 30° C. to 36° C.). For example, mutations such as TS 7 (Y942H/L1361C/L1558I mutations in the L protein), TS 12 (D433A/R434A/K437A mutations in the P protein), TS 13 (D433A/R434A/K437A mutations in the P protein and an L1558I mutation in the L protein), TS 14 (D433A/R434A/K437A mutations in the P protein and an L1361C mutation in the L protein), and TS 15 (D433A/R434A/K437A mutations in the P protein and L1361C/L1558I mutations in the L protein) of the Sendai virus are temperature-sensitive mutations, and may be suitably utilized in the present invention.

For those Sendai virus vectors, reference may be made to Japanese Patent Re-publication No. 2015/046229.

(Transcription Factor Required for Induction of Differentiation into Desired Cell Type)

The form of the "transcription factor required for induction of differentiation into the desired cell type" to be used in the method of the present invention is not particularly limited as long as the transcription factor can be carried on the Sendai virus vector, but examples thereof may include, but not particularly limited to, nucleic acids, such as RNA and DNA, and synthetic nucleic acids.

In addition, in the method of the present invention, examples of the desired cell type may include skeletal muscles (skeletal muscle cells), nerve cells (motor neurons and dopaminergic neurons), the liver (liver cells), chondrocytes, bone cells, and hematopoietic cells.

As described in Examples below, in the method of the present invention, differentiation can be performed by adding the transcription factor required for induction of differentiation into the desired cell type only once.

Further, as described in Examples below, in the method of the present invention, the number of kinds of required transcription factors has been successfully reduced as compared to related-art methods by carrying the transcription factor required for induction of differentiation into the desired cell type on the Sendai virus vector.

In addition, as described in Examples below, in the method of the present invention, the differentiation efficiency has been successfully improved as compared to related-art methods by carrying the transcription factor required for induction of differentiation into the desired cell type on the Sendai virus vector.

Besides, as described in Examples below, in the method of the present invention, the number of kinds of required transcription factors has been successfully reduced and the differentiation efficiency has been successfully improved as compared to related-art methods by: carrying the transcription factor required for induction of differentiation into the desired cell type on the Sendai virus vector; and adding a gene for a compound having an action of substantially removing or reducing an expression amount of a POU5F1 protein to the pluripotent stem cell.

(Method of Efficiently Inducing Differentiation of Pluripotent Stem Cell into Desired Cell Type of the Present Invention)

In the method of the present invention, a method of reducing the undifferentiation maintenance of a pluripotent stem cell, and as required, a method capable of reducing the differentiation resistance of a pluripotent stem cell to the desired cell type may be preferably introduced. Examples thereof may include the following.

(Pluripotent Stem Cell Whose Undifferentiation Maintenance has been Reduced)

In pluripotent stem cells, the expression of a transcription factor POU5F1 (SEQ ID NOS: 1 and 2: POU domain, class 5, transcription factor 1 isoform 1: ncbi.nlm.nih.gov/protein/NP_002692, other names: OCT3, OCT4, OTF3, OTF4, OTF-3, Oct-3, Oct-4, MGC22487) is essential to the undifferentiation maintenance of the pluripotent stem cells. POU5F1 is specifically expressed in pluripotent cells, such as reproductive cells and a preimplantation early embryo. That is, the "reducing the undifferentiation maintenance of a pluripotent stem cell" in the present invention means substantially removing or reducing an expression amount of a POU5F1 protein in the pluripotent stem cell. The substantially removing or reducing an expression amount of a POU5F1 protein encompasses inhibiting the process of any one of the transcription and translation stages of POU5F1 and/or inhibiting the activity of the translated POU5F1 protein, and is not particularly limited.

Besides, a state in which the expression amount of the POU5F1 protein in the pluripotent stem cell has been substantially removed or reduced may be confirmed by a comparison to the degree of the expression amount of the POU5F1 protein (or expression amount of the POU5F1 gene) in a pluripotent stem cell that has not been subjected to the removing or the reducing. For example, the state (degree) in which the expression amount of the POU5F1 protein in the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 15, from 30 to 20, or about 25 when compared to the expression amount of the POU5F1 protein in the pluripotent stem cell that has not been removed or reduced, which is defined as 100. The degree of the expression amount of the POU5F1 protein in the pluripotent stem cell may be easily measured by using a commercially available anti-POU5F1 antibody, and the gene expression amount of POU5F1 may be measured by a method known per se (see WO 2017/131238 A1).

(Reducing Differentiation Resistance of Pluripotent Stem Cell to Desired Cell Type)

In pluripotent stem cells, a special chromatin structure called a "bivalent domain" is formed in each promoter region of a group of genes involved in differentiation, and under a stemness-maintaining state, the group of genes involved in development/differentiation are in a standby state so as not to be easily expressed. The inventors of the present invention have confirmed that "when a methyl group modification of a histone called H3K27me3 is removed or reduced in the "bivalent domain", the expression of differentiation genes required for induction of differentiation into the desired cell type is rapidly and efficiently facilitated" (see WO 2017/073763 A1).

That is, the "reducing differentiation resistance of a pluripotent stem cell to a desired cell type" of the present invention means that the H3K27me3 modification of the pluripotent stem cell is substantially removed or reduced.

In addition, a state in which the H3K27me3 modification of the pluripotent stem cell has been substantially removed or reduced may be confirmed by a comparison to the degree of the H3K27me3 modification of a pluripotent stem cell that has not been subjected to the removing or the reducing. For example, the state (degree) in which the H3K27me3 modification of the pluripotent stem cell has been substantially removed or reduced is from 95 to 1, from 90 to 2, from 85 to 3, from 80 to 4, from 75 to 5, from 70 to 6, from 65 to 7, from 60 to 8, from 50 to 10, from 40 to 20, or about 30 when compared to the degree of the H3K27me3 modification of the pluripotent stem cell that has not been removed or reduced, which is defined as 100. The degree of the H3K27me3 modification of the pluripotent stem cell may be easily measured by using a commercially available anti-Histone H3K27me3 antibody, and the gene expression amount of H3K27me3 may be measured by a method known per se.

(Use of Modified Synthetic mRNA for Target Gene)

The method of the present invention preferably includes adding (introducing), to the pluripotent stem cell, a gene for a compound having an action of substantially removing or reducing an expression amount of a POU5F1 protein (a gene expressing small interfering RNA (siRNA) against POU5F1, a gene expressing shRNA against POU5F1, a gene expressing an antisense strand of POU5F1, or an antibody gene).

Similarly, the method of the present invention preferably includes adding (introducing), to the pluripotent stem cell, a gene for a compound having an action of substantially removing or reducing H3K27me3 modification.

The term "gene" as used herein encompasses not only double-stranded nucleic acids, but also their respective constituent single strands, such as plus strands (or sense strands) or complementary strands (or antisense strands), linear nucleic acids, and circular nucleic acids, and encompasses DNA, RNA, mRNA, cDNA, and the like, unless otherwise stated.

Besides, the target gene is meant to encompass the gene for the compound having an action of substantially removing or reducing an expression amount of a POU5F1 protein, and/or the gene for the compound having an action of substantially removing or reducing H3K27me3 modification, and the transcription factor required for induction of differentiation into the desired cell type.

A method known per se may be used without any particular limitation as a method of adding (introducing) the gene for the compound having an action of substantially removing or reducing an expression amount of a POU5F1 protein or the gene for the compound having an action of substantially removing or reducing H3K27me3 modification to the pluripotent stem cell. There is preferably used a method of inducing differentiation by efficiently introducing synthetic mRNA into human pluripotent stem cells through use of a gene expression method involving using synthetic mRNA developed by Warren, Rossi, et al. (reference: Cell Stem Cell 7: 618-630, 2010.), which is a footprint-free forced gene expression method causing no gene incorporation into a host genome (see WO 2017/131238 A1).

The timing, at which the gene for the compound having an action of substantially removing or reducing an expression amount of a POU5F1 protein (or the gene for the compound having an action of substantially removing or reducing H3K27me3 modification) and the Sendai virus vector containing the transcription factor required for induction of differentiation into the desired cell type are added to the pluripotent stem cell, is not particularly limited. It is preferred that the gene for the compound having an action of substantially removing or reducing an expression amount of a POU5F1 protein (or the gene for the compound having an action of substantially removing or reducing H3K27me3 modification) be added to the pluripotent stem cell after the addition of the Sendai virus vector containing the transcription factor required for induction of differentiation into the desired cell type.

Further, the timing and number of times of the addition of each gene (mRNA) are not particularly limited. In the method of the present invention, unlike the related art, differentiation can be performed with high efficiency by adding the transcription factor required for induction of differentiation into the desired cell type (Sendai virus vector containing the transcription factor required for induction of differentiation into the desired cell type), and as required, the gene for the compound having an action of substantially removing or reducing an expression amount of a POU5F1 protein once during culture.

(Synthesis of Modified mRNA Encoding Amino Acid Sequence of Transcription Factor)

Modified mRNA is synthesized with reference to a method described in the literature "Warren et al., Cell Stem Cell, 2010 Nov. 5; 7 (5): 618-30." More specifically, mRNA is synthesized by in vitro transcription using a mixture of dNTPs {(dNTPs: 3-O-Me-m$^7$G(5')ppp(5')G ARCA cap analog, 5-methylcytidine triphosphate, and pseudouridine triphosphate)} obtained by modifying template DNA encoding the amino acid sequence of the transcription factor required for induction of differentiation into the desired cell type.

(Generation of Sendai Virus Vector Encoding Transcription Factor Required for Induction of Differentiation into Desired Cell Type)

In the present invention, the Sendai virus vector is used for the introduction of the transcription factor required for induction of differentiation into the desired cell type. Further, in order to express a mammalian (in particular, human) transcription factor, a Sendai virus vector capable of expressing a human transcription factor is preferably used. In particular, a mutant of a Sendai virus vector, such as an F protein-deficient mutant, has no infectivity, and hence is easy to handle (see Inoue et al., J Virol. 77.5: [2]3238-3246, 2003).

(Method of Inducing Differentiation of Pluripotent Stem Cell into Desired Cell Type with High Efficiency)

A single transcription factor or a cocktail of two or more transcription factors required for induction of differentiation into the desired cell type is prepared. The form of the transcription factor is a Sendai virus vector having incorporated therein a transcription factor (or a plurality of transcription factors).
(Use of Expression Vector)

In a step of the method of the present invention, there may be used an expression vector known per se having introduced therein the gene for the compound having an action of substantially removing or reducing an expression amount of a POU5F1 protein (or the gene for the compound having an action of substantially removing or reducing H3K27me3 modification) and/or the transcription factor required for induction of differentiation into the desired cell type. An example of the expression vector to be used in the present invention may be a Sendai virus vector.

A method of introducing the expression vector into the pluripotent stem cell is not particularly limited, but examples thereof may include a lipofection method, a liposome method, an electroporation method, a calcium phosphate coprecipitation method, a diethylaminoethyl (DEAE)-dextran method, a microinjection method, and a gene gun method. A particularly preferred example is a lipofection method.

As another method, the gene for the compound having an action of substantially removing or reducing an expression amount of a POU5F1 protein (or the gene for the compound having an action of substantially removing or reducing H3K27me3 modification) may be converted to cationic siRNA by binding spermine, phosphospermine, or the like thereto. The cationic siRNA does not require a reagent for transfection.

(Compound Having Action of Substantially Removing or Reducing Expression Amount of POU5F1 Protein)

The compound having an action of substantially removing or reducing an expression amount of a POU5F1 protein of the present invention is not particularly limited, but is, for example, siRNA against POU5F1, shRNA against POU5F1, an antisense strand of POU5F1, an antibody that specifically binds to the POU5F1 protein, or an inhibitor.

In addition, not only by using those compounds alone, but by using a plurality of kinds of compounds and/or a low-molecular-weight compound in combination, it is possible to efficiently "reduce the undifferentiation maintenance of a pluripotent stem cell (substantially remove or reduce an expression amount of a POU5F1 protein of a pluripotent stem cell)."

(Compound Having Action of Substantially Removing or Reducing H3K27Me3 Modification)

The compound having an action of substantially removing or reducing H3K27me3 modification of the present invention is not particularly limited, but is, for example, a demethylase (in particular, a demethylase having an action of removing a methyl group of H3K27me3), an antibody that specifically binds to H3K27me3, an antibody for Polycomb-group proteins (PcG proteins) having an H3K27me3 modification action, siRNA (in particular, cationic siRNA), or an inhibitor. The cationic siRNA does not require a reagent for transfection.

Examples of the compound may include low-molecular-weight compounds including, but not particularly limited to, histone deacetylase (HDAC) inhibitors, such as valproic acid.

(JMJD3)

JMJD3 is known as a demethylase for H3K27me3 of a histone (mouse NP_001017426, human NP_001073893), and even in its full length (NP_001073893, SEQ ID NO: 3), has an action of substantially removing or reducing the H3K27me3 modification of pluripotent stem cells. The inventors of the present invention have confirmed that JMJD3c having the JmjC domain {SEQ ID NO: 4, catalytic domain: SEQ ID NO: 5 (amino acids 1376-1484)} has a stronger action of substantially removing or reducing H3K27me3 modification as compared to full-length JMJD3 (see WO 2017/073763 A1).

A preferred base sequence of JMJD3 is a base sequence set forth in SEQ ID NO: 6.

(Kind of Transcription Factor Required for Induction of Differentiation into Desired Cell Type)

The form of the "transcription factor required for induction of differentiation into the desired cell type" to be used in the method of the present invention is not particularly limited as long as the transcription factor can be carried on the Sendai virus vector, but examples thereof may include, but not particularly limited to, nucleic acids, such as RNA and DNA, and synthetic nucleic acids.

In addition, in the method of the present invention, examples of the desired cell type may include skeletal muscles (skeletal muscle cells), the liver (liver cells), nerve cells (motor neurons and dopaminergic neurons), chondrocytes, bone cells, and hematopoietic cells.

As described in Examples below, in the method of the present invention, the number of kinds of transcription factors required for induction of differentiation into the desired cell type has been successfully reduced and/or high differentiation efficiency has been successfully achieved by carrying the transcription factor required for induction of differentiation into the desired cell type on the Sendai virus vector.

{Transcription Factor Required for Induction of Differentiation into Skeletal Muscle (in Particular, Cells Present in Skeletal Muscle)}

A method of inducing differentiation into a skeletal muscle is as described below.

A single transcription factor, or two or more transcription factors selected from the group consisting of MYOD1, NRF1, SALL4, ZIC1, KLF9, ZNF281, CTCF, HES1, HOXA2, TBX5, TP73, ERG, MAB21L3, PRDM1, NFIC, CTCFL, FOXP1, HEY1, PITX2, JUNB, KLF4, ESX1, TFAP2C, FOS, TFE3, FOSL1, GRHL2, TBX2, NFIB, and IRF4 are introduced into pluripotent stem cells. In particular, MYOD1 (base sequence: SEQ ID NO: 7, amino acid sequence: SEQ ID NO: 8) is preferably introduced alone into pluripotent stem cells.

(Transcription Factor Required for Induction of Differentiation into Nerve Cells)

A method of inducing differentiation into nerve cells (in particular, motor neurons or dopaminergic neurons) is as described below.

A single transcription factor, or two, three, four, five, or six transcription factors selected from NEUROG1, NEUROG2, NEUROG3, NEUROD1, NEUROD2, and FOXA1 are introduced into human pluripotent stem cells.

For example, for the motor neurons (cholinergic and/or motor neurons), NEUROG3 (NGN3) (base sequence: SEQ ID NO: 9, amino acid sequence: SEQ ID NO: 10) is preferably introduced alone into pluripotent stem cells.

For example, for the dopaminergic neurons, FOXA1 (accession number: NM 004496) is preferably introduced alone into pluripotent stem cells.

{Transcription Factor Required for Induction of Differentiation into Liver (in Particular, Cells Present in Liver, i.e., Hepatoblasts)}

A method of inducing differentiation into the liver (in particular, the liver or the fetal liver) is as described below.

For the liver, only one transcription factor, or two or more transcription factors selected from HNF1A, TCF-1, SALL4, TGIF1, MAB21L3, ZIC1, EGFLAM, PITX2, HNF4A, NRF1, ZNF281, CTCFL, TP73, TFE3, DLX6, and TCF4 are introduced into human pluripotent stem cells.

For the fetal liver, only one transcription factor, or two or more transcription factors selected from HNF1A, TCF-1, SIX5, HNF4A, SIN3A, ID1, and HNF1A are introduced into human pluripotent stem cells.

In particular, the FOXA1 gene and HNF1A (base sequence: SEQ ID NO: 11, amino acid sequence: SEQ ID NO: 12) are preferably introduced into pluripotent stem cells.

(Transcription Factor Required for Induction of Differentiation into Hematopoietic Cells)

A method of inducing differentiation into hematopoietic cells is as described below.

Only one transcription factor, or two, three, four, five, six, or seven transcription factors selected from CDYL2, ETS2, SPI1, OVOL2, CDX2, CEBPB, and SALL4 are introduced into human pluripotent stem cells.

In particular, SPI1 (base sequence: SEQ ID NO: 18, amino acid sequence: SEQ ID NO: 19) is preferably introduced into pluripotent stem cells.

(Method of Introducing Target Gene into Genome of Pluripotent Stem Cell)

In a step of the method of the present invention, a method known per se may be used without any particular limitation as a method of introducing the gene for the compound having an action of substantially removing or reducing an expression amount of a POU5F1 protein (or the gene for the compound having an action of substantially removing or reducing H3K27me3 modification) into the genome of the pluripotent stem cell. There may be preferably used an expression cassette inserted between PiggyBac transposase recognition sequences (PB sequences) developed by Woltjen et al. (reference: Nature 458: 766-770, 2009.), which is a mechanism by which a gene to be introduced is actively incorporated into pluripotent stem cells (in particular, the genome of human ES cells). The expression cassette is a system capable of efficiently establishing a genetically modified pluripotent stem cell line by introducing a drug selection cassette (see WO 2017/131238 A1).

(Method of Introducing Target Protein into Pluripotent Stem Cell)

In a step of the method of the present invention, a method known per se may be used as a method of introducing (transfecting) the compound having an action of substantially removing or reducing an expression amount of a POU5F1 protein (or the compound having an action of substantially removing or reducing H3K27me3 modification) (in particular, a protein) into the pluripotent stem cell, and examples thereof may include: a method involving using a protein transfection reagent; a method involving using a fusion protein having added thereto a cell-penetrating peptide; and a microinjection method.

The "cell-penetrating peptide" in the present invention is a peptide having a property of migrating into a cell, more specifically a property of penetrating a cell membrane, still more specifically a property of penetrating a cell membrane or a nuclear membrane to penetrate into cytoplasm or a nucleus. The amino acid sequence of the peptide is not particularly limited, but examples thereof may include TAT (GRKKRRQRRRPQ: SEQ ID NO: 13), r8 {rrrrrrrr (D-form-R): SEQ ID NO: 14}, and MPG-8 (BAFLGWL-GAWGTMGWSPKKKRK: SEQ ID NO: 15).

The target protein encompasses the compound having an action of substantially removing or reducing an expression amount of a POU5F1 protein (or the compound having an action of substantially removing or reducing H3K27me3 modification) (in particular, a protein).

(Gene Knockout Method)

A gene knockout method is available as a method other than the foregoing. A "pluripotent stem cell in which a POU5F1 gene has been disrupted" may be generated by the gene knockout method. The "pluripotent stem cell in which a POU5F1 gene has been disrupted" means that normal expression of the POU5F1 gene is inhibited due to artificial modification of the sequence of a POU5F1 gene region, and as a result, the expression of POU5F1 is suppressed and a POU5F1 protein is not normally expressed.

In addition, the "whole" in "modification or deletion of part or the whole of the POU5F1 gene" refers to the protein-coding region of POU5F1 genomic DNA.

In addition, the "part" refers to a region that is part of the protein-coding region and that has a length required for inhibiting normal expression of the POU5F1 gene.

Further, the "modification" refers to modification of the base sequence of a target region in genomic DNA into another base sequence by substituting, deleting, inserting, and/or adding a single nucleotide or a plurality of nucleotides.

(Differentiation Induction Kit for Inducing Differentiation of Pluripotent Stem Cell into Desired Cell Type with High Efficiency)

A differentiation induction kit for efficiently inducing differentiation of a pluripotent stem cell into a desired cell type of the present invention (hereinafter sometimes referred to as "kit of the present invention") includes any one or more of the following items (1) to (5) in addition to a transcription factor required for induction of differentiation into the desired cell type and a Sendai virus vector.

(1) Pluripotent Stem Cell in which Expression Amount of POU5F1 Protein has been Substantially Removed or Reduced and/or H3K27Me3 Modification has been Substantially Removed or Reduced A user can easily induce differentiation into the desired cell type by, as described above, introducing a Sendai virus vector containing a transcription factor required for induction of differentiation into the desired cell type into a pluripotent stem cell in which an expression amount of a POU5F1 protein has been substantially removed or reduced and/or H3K27me3 modification has been substantially removed or reduced.

In addition, such pluripotent stem cell encompasses a pluripotent stem cell having a gene construct inducible with doxycycline or the like inserted into the genome thereof so that a gene for a compound having an action of substantially removing or reducing an expression amount of a POU5F1 protein, a demethylase, or the like can be transiently forcibly expressed therein.

(2) Gene for Compound Having Action of Substantially Removing or Reducing Expression Amount of POU5F1 Protein and/or Demethylase Gene for Kit of the Present Invention The user can easily generate the pluripotent stem cell in which an expression amount of a POU5F1 protein has been substantially removed or reduced and/or H3K27me3 modification has been substantially removed or reduced by adding a gene for a compound having an action of substantially removing or reducing an expression amount of a POU5F1 protein and/or a demethylase gene for a kit to a pluripotent stem cell.

Examples of anti-POU5F1 antibody gene may include, but not particularly limited to, commercially available antibody genes.

Examples of the demethylase gene for a kit may include, but not particularly limited to, mRNAs, DNAs, and proteins of demethylase genes (e.g., JMJD3c).

(3) Gene for Compound Having Action of Substantially Removing or Reducing Expression Amount of POU5F1 Protein and/or Demethylase Gene, and Sendai Virus Vector Containing Transcription Factor Required for Induction of Differentiation into Desired Cell Type for Kit of the Present Invention The user can easily generate the pluripotent stem cell in which an expression amount of a POU5F1 protein has been substantially removed or reduced and/or H3K27me3 modification has been substantially removed or reduced, and further, can induce differentiation thereof into the desired cell type with high efficiency by adding a gene for a compound having an action of substantially removing or reducing an expression amount of a POU5F1 protein and/or a demethylase gene, and a Sendai virus vector containing a transcription factor required for induction of differentiation into the desired cell type for a kit to a pluripotent stem cell.

Those genes may exist on one gene, or on separate genes. When the genes are present on separate genes, the gene for the compound having an action of substantially removing or reducing an expression amount of a POU5F1 protein (or the demethylase gene) and the Sendai virus vector containing the transcription factor required for induction of differentiation into the desired cell type may be added to the pluripotent stem cell simultaneously or at separate times.

(4) Compound Having Action of Substantially Removing or Reducing Expression Amount of POU5F1 Protein and/or Demethylase for Kit of the Present Invention The user can easily generate the pluripotent stem cell in which an expression amount of a POU5F1 protein has been substantially removed or reduced and/or H3K27me3 modification has been substantially removed or reduced by adding a compound having an action of substantially removing or reducing an expression amount of a POU5F1 protein and/or a demethylase for a kit to the pluripotent stem cell.

(5) Gene Construct Carrying Gene for Compound Having Action of Substantially Removing or Reducing Expression Amount of POU5F1 Protein and/or Demethylase Gene The user can easily generate the pluripotent stem cell in which an expression amount of a POU5F1 protein has been substantially removed or reduced and/or H3K27me3 modification has been substantially removed or reduced by introducing a gene construct carrying a gene for a compound having an action of substantially removing or reducing an expression amount of a POU5F1 protein and/or a demethylase gene into the genome of a pluripotent stem cell.

The gene construct may contain a promoter sequence, a gene expression-enhancing sequence, a marker gene, a reporter sequence, a drug resistance gene, and the like as required in addition to the gene for the compound having an action of substantially removing or reducing an expression amount of a POU5F1 protein and/or the demethylase gene.

A method of the present invention may be exemplified by, but not particularly limited to, a method including any one of the following steps (1) to (8):

(1) a step of adding a gene for a compound having an action of substantially removing or reducing an expression amount of a POU5F1 protein and a Sendai virus vector containing a transcription factor required for induction of differentiation into the desired cell type to a pluripotent stem cell;

(2) a step of inserting a gene construct carrying a gene for a compound having an action of substantially removing or reducing an expression amount of a POU5F1 protein and a Sendai virus vector containing a transcription factor required for induction of differentiation into the desired cell type into the genome of a pluripotent stem cell;

(3) a step of adding a Sendai virus vector containing a transcription factor required for induction of differentiation into the desired cell type to a pluripotent stem cell in which an expression amount of a POU5F1 protein has been substantially removed or reduced;

(4) a step of adding a Sendai virus vector containing a transcription factor required for induction of differentiation into the desired cell type to a pluripotent stem cell in which a compound having an action of substantially removing or reducing an expression amount of a POU5F1 protein is forcibly expressed;

(5) a step of adding a compound having an action of substantially removing or reducing an expression amount of a POU5F1 protein and a Sendai virus vector containing a transcription factor required for induction of differentiation into the desired cell type to a pluripotent stem cell;

(6) a step of adding a Sendai virus vector containing a transcription factor required for induction of differentiation into the desired cell type to a pluripotent stem cell in which a POU5F1 gene has been disrupted;

(7) a step of adding a gene for a compound having an action of substantially removing or reducing an expression amount of a POU5F1 protein, a demethylase gene, and a Sendai virus vector containing a transcription factor required for induction of differentiation into the desired cell type to a pluripotent stem cell; and (8) a step of adding a Sendai virus vector containing a transcription factor required for induction of differentiation into the desired cell type to a pluripotent stem cell in which an expression amount of a POU5F1 protein has been substantially removed or reduced and which has a histone in which H3K27me3 modification has been substantially removed or reduced.

In the method of the present invention, any one of the following pluripotent stem cells for differentiation into the desired cell type may also be used:

(1) a pluripotent stem cell for differentiation into the desired cell type, in which an expression amount of a POU5F1 protein has been substantially removed or reduced;

(2) a pluripotent stem cell for differentiation into the desired cell type, in which a gene for a compound having an action of substantially removing or reducing an expression amount of a POU5F1 protein is forcibly expressed;

(3) a pluripotent stem cell for differentiation into the desired cell type, which has a gene construct carrying a gene for a compound having an action of substantially removing or reducing an expression amount of a POU5F1 protein inserted into the genome thereof;

(4) a pluripotent stem cell for differentiation into the desired cell type, in which a POU5F1 gene has been disrupted; and (5) a pluripotent stem cell for differentiation into the desired cell type, in which an expression amount of a POU5F1 protein has been substantially removed or reduced and which has a histone in which H3K27me3 modification has been substantially removed or reduced.

EXAMPLES

The present invention is described below by way of Examples, but the present invention is by no means limited to Examples.

Example 1

(Differentiation into Skeletal Muscles)

In this Example, it was confirmed that, through the use of a temperature-sensitive Sendai virus vector expressing a human MYOD1 gene, hPSCs were able to be differentiated into skeletal muscles within 1 week. In this Example, it was also confirmed that the addition of siPOU5F1, which suppressed the expression of a pluripotency gene POU5F1 (also known as OCT4 or OCT3/4), further enhanced differentiation efficiency.

(Materials and Methods)

<Cell Culture>

An iPSC line derived from human adipose stem cells (iPSCs-ADSC) was obtained from System Biosciences (Palo Alto). Cells were maintained as undifferentiated pluripotent cells in accordance with a standard hPSC culture method involving using StemFit basic02 (Ajinomoto) supplemented with 100 ng/ml FGF2. The cells were cultured on a cell culture dish coated with lamin-511 (iMatrix-511, Nippi). For skeletal muscle differentiation, α-MEM (Thermo-Fisher) supplemented with 5% KSR (Thermo-Fisher) was used as a culture medium.

<Sendai Virus Vector>

A temperature-sensitive Sendai virus vector expressing human MYOD1 (SeV18+hMYOD1/TS15AF) was custom-made by ID Pharma on contract. This Sendai virus vector is F protein-deficient, and hence is nontransmissible (Inoue et al., J Virol. 77.5: 3238-3246, 2003). This Sendai virus vector is temperature-sensitive, and this virus functions at 33° C. and is inactivated at 37° C. (Ban et al., Proc Natl Acad Sci USA. 2011; 108(34): 14234-14239).

A stock solution of the Sendai virus vector was diluted to $1 \times 10^4$ cell-infecting units (CIU)/μl.

<Phosphospermine-Bound siPOU5F1>

In order to suppress the expression of human POU5F1 in the hPSCs, small interfering RNAs (siRNAs) against human POU5F1 were designed and used. In order to introduce the siRNAs without using lipofection or any other cationic lipid-based transfection reagent, the siRNAs were bound with phosphospermine (Paris et al., Molecular Pharmaceutics 2012. 9: 3464-3475). Sequences used are a human POU5F1 sense strand: 5'-GCCCGAAAGAGAAAGCGAAdT*dT-3' (SEQ ID NO: 16) and a human POU5F1 antisense strand: 5'-UUCGC-UUUCUCUUUCGGGCdCdT-3' (SEQ ID NO: 17). The sense strand has 19 RNA bases and 2 DNA bases having added thereto 30 spermine molecules at the site indicated by *. The antisense strand has 19 RNA bases and 2 DNA bases. The sense strand and the antisense strand were annealed, and stored as a 100 μM stock solution.

<Procedure>

(1) On Day 1, the human iPSCs (iPSCs-ADSC line) were plated in a 24-well plate or a 4-well plate at $1.0 \times 10^5$ cells in 250 μl of the medium per well. The culture medium used was α-MEM (Thermo-Fisher) supplemented with 5% KSR (Thermo-Fisher). Immediately after the plating, the Sendai virus vector encoding the human MYOD1 gene was added to the cell culture medium at a multiplicity of infection (MOI) of 2.5. In this Example, 25 μl of a Sendai virus solution containing $2.5 \times 10^5$ CIU was added to 250 μl of the medium containing $1.0 \times 10^5$ cells. One hour after the addition of the Sendai virus vector, 1 ml of a culture solution was added to a total amount of 1.275 ml per well. The cells were cultured in a $CO_2$ incubator at 33° C., a permissive temperature for viral replication and gene expression. The culture medium (1 ml/well) was changed daily.

(2) On Day 2, 4 μl of phosphospermine-siPOU5F1 (100 μM stock solution) was added to 1 ml of the medium per well at a final concentration of 400 nM.

(3) On Day 4, the temperature of the $CO_2$ incubator was changed to 37° C., a non-permissive temperature for viral replication and gene expression.

(4) On Day 5, spindle-shaped cells serving as a clear indication of skeletal muscle differentiation were observed.

(5) On Day 6, the cells were fixed, and the efficiency of cell differentiation was evaluated using immunostaining. The immunostaining was performed by incubating the fixed cells overnight using an anti-myosin heavy chain (MHC) antibody (R&D systems) in 1:400 dilution. The cells were incubated for 1 hour using Alexa fluor 555 goat anti-mouse IgG as a secondary antibody in 1:200 dilution.

In FIG. 1A, a typical experimental procedure of the method of differentiating hPSCs into skeletal muscles according to the present invention is illustrated.

(Results)

Figure 1C:
Figure 1B:

FIG. 1B is an example of a microscopic image (10× objective lens) of the cells immunostained with anti-myosin heavy chain (MHC) (red signal), which is specific for mature skeletal muscles. The cells were stained with DAPI (green signal) for visualizing the nuclei of all cells. An enlarged microscopic image (20× objective lens) of the cells is shown in FIG. 1C. Highly efficient formation of skeletal muscle cells was shown in visual inspection of the immunostaining result. By counting DAPI-positive cells and MHC-positive cells in a total of five images, it was found the average fraction (average differentiation efficiency) of the MHC-positive cells in the DAPI-positive cells was 84.7% (528 cells/623 cells). This average differentiation efficiency was the highest efficiency of skeletal muscle differentiation from hPSCs in the hitherto reported results. In addition, in the method of the present invention, an efficiency of skeletal muscle differentiation of 90% or more was observed.

As apparent from the above-mentioned results, the method of the present invention was able to achieve differentiation of hPSCs into skeletal muscle cells rapidly (5 days), efficiently and homogeneously (up to about 85% of MHC-positive skeletal muscle cells in all cells during culture), and simply (only one time of treatment with the Sendai virus vector, and only one time of treatment with phosphospermine-siPOU5F1). In Table 1, a comparison between the method of the present invention and related-art methods is shown.

TABLE 1

| Method | Speed (days) | Efficiency (% MHC-positive cells) | Effect |
|---|---|---|---|
| The present invention | 5 | ~85% | One time of Sendai virus infection; one time of phosphospermine-siPOU5F1 treatment. One kind of cell culture medium. |

TABLE 1-continued

| Method | Speed (days) | Efficiency (% MHC-positive cells) | Effect |
|---|---|---|---|
| Synthetic mRNA cocktail (Akiyama et al., Development. 2016; 143: 3674-3685) | 5 | ~65% | Five times of transfection with synthetic mRNA cocktail. Two kinds of cell culture media. |
| Successive changes in cell culture environment (medium). AMSBIO (amsbio.com) Skeletal muscle differentiation kit | 20 | ~70% | Three kinds of cell culture media. |

As apparent from the foregoing, as compared to the related-art methods, the method of the present invention is a method capable of achieving a skeletal muscle cell differentiation efficiency of from about 71% or more to about 90% or less, from about 73% or more to about 90% or less, from about 75% or more to about 90% or less, from about 78% or more to about 90% or less, from about 80% or more to about 90% or less, from about 82% or more to about 90% or less, from about 83% or more to about 90% or less, from about 84% or more to about 90% or less, from about 85% to about 90% or less, about 85%, about 90%, or about 90% or more with one kind of medium and through one time of transcription factor introduction. Further, the method of the present invention is a method capable of achieving the above-mentioned differentiation efficiency within 12 days, within 10 days, within 9 days, within 8 days, within 7 days, within 6 days, or within 5 days.

Example 2

(Differentiation into Motor Neurons)

In this Example, it was confirmed that, through the use of a temperature-sensitive Sendai virus vector expressing a human NGN3 gene, hPSCs were able to be differentiated into cholinergic and/or motor neurons within 1 week.

(Materials and Methods)

<Cell Culture>

An iPSC line derived from human adipose stem cells (iPSCs-ADSC) was obtained from System Biosciences (Palo Alto). Cells were maintained as undifferentiated pluripotent cells in accordance with a standard hPSC culture method involving using StemFit basic02 (Ajinomoto) supplemented with 100 ng/ml FGF2. The cells were cultured on a cell culture dish coated with lamin-511 (iMatrix-511, Nippi). For motor neuron differentiation, a 1:1 mixture of DMEM/F12 HAM and Neurobasal medium was used as a cell culture medium. The medium was supplemented with 1×N2/B27, dorsomorphin (final concentration: 3.3 µM), SB431542 (final concentration: 3.3 µM), and forskolin (final concentration: 3.3 µM).

<Sendai Virus Vector>

A temperature-sensitive Sendai virus vector expressing human NGN3 (SeV18+hNGN3/TS15ΔF) was custom-made by ID Pharma on contract. This Sendai virus vector is F protein-deficient, and hence is nontransmissible. This Sendai virus vector is temperature-sensitive, and this virus functions at 33° C. and is inactivated at 37° C. A stock solution of the Sendai virus vector was diluted to $1×10^4$ CIU/µl.

<Procedure>

(1) On Day 1, the human iPSCs (iPSCs-ADSC line) were plated in a 24-well plate or a 4-well plate at $1.0×10^5$ cells in 250 µl of the medium per well. The culture medium is as described above (1:1 mixture of DMEM/F12 HAM and Neurobasal medium supplemented with 1×N2/B27, dorsomorphin, SB431542, and forskolin). Immediately after the plating, the Sendai virus vector encoding the human NGN3 gene was added to the cell culture medium at a multiplicity of infection (MOI) of 2.5. In this Example, 25 µl of a Sendai virus solution containing $2.5×10^5$ CIU was added to 250 µl of the medium containing $1.0×10^5$ cells. One hour after the addition of the Sendai virus vector, 1 ml of a culture solution was added to a total amount of 1.275 ml per well. The cells were cultured in a $CO_2$ incubator at 33° C., a permissive temperature for viral replication and gene expression. The culture medium (1 ml/well) was changed daily
(2) On Day 3, the temperature of the $CO_2$ incubator was changed to 37° C., a non-permissive temperature for viral replication and gene expression.
(3) As an optional procedure, on Day 4, the cells were passaged, and cultured on an ornithine/laminin-coated glass coverslip so that differentiated neurons were easily visible under a microscope.
(4) On Day 6, the cells were fixed, and the efficiency of cell differentiation was evaluated using immunostaining. The immunostaining was performed by incubating the fixed cells overnight using an anti-tubulin β3 (TUBB3) antibody or anti-choline acetyltransferase (ChAT) antibody.

In FIG. 2A, a typical experimental procedure of the method of differentiating hPSCs into neurons according to the present invention is illustrated.

(Results)

FIG. 2B to FIG. 2D are examples of microscopic images (20× objective lens) of the immunostained cells. FIG. 2B is an image of the cells stained with DAPI (blue signal) for visualizing the nuclei of all cells. FIG. 2C is an image of the cells immunostained with anti-β3-tubulin (TUBB3) antibody (red signal), which is specific for mature neurons. FIG. 2D is an image of the cells immunostained with anti-choline acetyltransferase (ChAT) antibody (green signal), which is specific for motor neurons. FIG. 2E is a synthetic image of FIG. 2C and FIG. 2D. By counting DAPI-positive cells and TUBB3-positive cells in a total of five images, it was found that the average fraction of the TUBB3-positive cells in the DAPI-positive cells (average differentiation efficiency) was 89.5% (205 cells/229 cells). This result of average differentiation efficiency shows that the method of the present invention can produce up to about 90% of neurons from hPSCs. By counting ChAT-positive cells and TUBB3-positive cells in a total of five images, it was found that the average fraction of the ChAT-positive cells in the TUBB3-positive cells was 93.2% (191 cells/205 cells). This result shows that most of the neurons produced using the combination of the Sendai virus vector expressing NGN3 and the differentiation medium are motor neurons. The efficiency was confirmed to be the highest efficiency of motor neuron differentiation from hPSCs in the hitherto reported results.

As apparent from the above-mentioned results, the method of the present invention was able to achieve differentiation of hPSCs into motor neurons rapidly (5 days), efficiently and homogeneously (up to about 90% of TUBB3-positive neurons in all cells during culture), and simply (only one time of treatment with the Sendai virus vector). In Table 2, a comparison between the method of the present invention and related-art methods is shown.

TABLE 2

| Method | Speed (days) | Efficiency (% TUBB3-positive cells) | Effect |
|---|---|---|---|
| The present invention | 5 | ~90% | One time of Sendai virus infection. One kind of cell culture medium. |
| Synthetic mRNA cocktail (Goparaju et al., Scientific Reports. 2017; 7: 42367) | 5 | ~90% | Two to four times of transfection with synthetic mRNA cocktail. Two kinds of cell culture media. |
| Successive changes in cell culture environment (medium) (Chambers et al. 2012. Nature Biotech 7: 715.) | 10 | ~75% | Five kinds of cell culture media. |

As apparent from the foregoing, as compared to the related-art methods, the method of the present invention is a method capable of achieving a motor neuron differentiation efficiency of from about 76% or more to about 90% or less, from about 78% or more to about 90% or less, from about 80% or more to about 90% or less, from about 82% or more to about 90% or less, from about 84% or more to about 90% or less, from about 86% or more to about 90% or less, from about 88% or more to about 90% or less, or about 90% with one kind of medium and through one time of transcription factor introduction. Further, the method of the present invention is a method capable of achieving the above-mentioned differentiation efficiency within 12 days, within 10 days, within 9 days, within 8 days, within 7 days, within 6 days, or within 5 days.

Example 3

(Differentiation into Liver Cells)

In this Example, it was confirmed that a temperature-sensitive Sendai virus vector expressing a human FOXA1 gene and/or an HNF1A gene was able to differentiate hPSCs into liver cells.

(Materials and Methods)

<Cell Culture>

An iPSC line derived from human adipose stem cells (iPSCs-ADSC) was obtained from System Biosciences (Palo Alto). Cells were maintained as undifferentiated pluripotent cells in accordance with a standard hPSC culture method involving using StemFit basic02 (Ajinomoto) supplemented with 100 ng/ml FGF2. The cells were cultured on a cell culture dish coated with lamin-511 (iMatrix-511, Nippi). For liver cell differentiation, media described in the literature (Hay et al., Stem Cells. 2008, 26: 894-902 and Kajiwara et al., Proc Natl Acad Sci USA. 2012, 109: 14716) were used. Both cases in the literature took 18 days for differentiation, and used four kinds of cell culture media, i.e., priming medium A (1 day), priming medium B (3 days), differentiation medium (7 days), and maturation medium (7 days). On the other hand, as described below, the method of the present invention took only 8 days for differentiation, and used only two kinds of differentiation media, i.e., differentiation medium (5 days) and maturation medium (1 day).

<Sendai Virus Vector>

A temperature-sensitive Sendai virus vector expressing human HNF1A (SeV18+hHNF1A/TS15ΔF) and a temperature-sensitive Sendai virus vector expressing FOXA1 (SeV18+hFOXA1/TS15ΔF) were custom-made by ID Pharma on contract. This Sendai virus vector is F protein-deficient, and hence is nontransmissible. This Sendai virus vector is temperature-sensitive, and this virus functions at 33° C. and is inactivated at 37° C. A stock solution of the Sendai virus vector was diluted to $1\times10^4$ CIU/μl.

<Phosphospermine-Bound siPOU5F1>

In order to suppress the expression of human POU5F1 in the hPSCs, small interfering RNAs (siRNAs) against human POU5F1 were designed and used. In order to introduce the siRNAs without using lipofection or any other cationic lipid-based transfection reagent, the siRNAs were bound with phosphospermine (Paris et al., Molecular Pharmaceutics 2012. 9: 3464-3475). Sequences used are a human POU5F1 sense strand: 5'-GCCCGAAAGAGAAAGCGAAdT*dT-3' (SEQ ID NO: 16) and a human POU5F1 antisense strand: 5'-UUCGC-UUUCUCUUUCGGGCdCdT-3' (SEQ ID NO: 17). The sense strand has 19 RNA bases and 2 DNA bases having added thereto 30 spermine molecules at the site indicated by *. The antisense strand has 19 RNA bases and 2 DNA bases. The sense strand and the antisense strand were annealed, and stored as a 100 μM stock solution.

<Procedure>

(1) On Day 1, the human iPSCs (iPSCs-ADSC line) were plated in a 24-well plate or a 4-well plate at $1.0\times10^5$ cells in 250 μl of the medium per well. The cell culture medium used was a ROCK inhibitor (Y27632)-containing StemFit (registered trademark in Japan) Basic02 (Ajinomoto). Immediately after the plating, a mixture of the Sendai virus vector encoding the human HNF1A gene (25 μl of a Sendai virus solution containing $2.5\times10^5$ CIU) and the FOXA1 gene (25 μl of a Sendai virus solution containing $2.5\times10^5$ CIU) was added to the cell culture medium. One hour after the addition of the Sendai virus vector, 1 ml of a culture solution was added to a total amount of 1.30 ml per well. The cells were cultured in a $CO_2$ incubator at 33° C., a permissive temperature for viral replication and gene expression. The culture medium (1 ml/well) was changed daily.

(2) On Day 2, 4 μl of phosphospermine-siPOU5F1 (100 μM stock solution) was added to 1 ml of the medium per well at a final concentration of 400 nM.

(3) On Day 2, the cell culture medium was replaced with a differentiation medium containing 1% DMSO.

(4) On Day 5, the temperature of the $CO_2$ incubator was changed to 37° C., a non-permissive temperature for viral replication and gene expression.

(5) On Day 7, the cell culture medium was replaced with a maturation medium containing L15 medium supplemented with 20 ng/ml hepatocyte growth factor (HGF), 20 ng/ml oncostatin M (OSM), 1 μM dexamethasone, 10 μM SB431542, 10 μM ROCK inhibitor, and 0.1 mg/ml ascorbic acid.

(6) On Day 8, the cells were fixed, and the efficiency of cell differentiation was evaluated using immunostaining. The immunostaining was performed by incubating the fixed cells using an anti-albumin antibody.

Figure 3A:
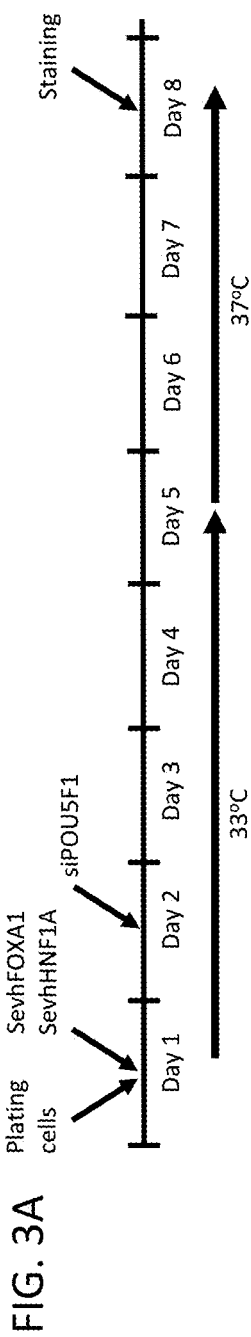
FIG. 3A, FIG. 3B, FIG. 3C, FIG. 3D, and FIG. 3E are a schematic and images for illustrating and showing differentiation into liver cells.
Figures 3B, 3C, 3D, 3E:
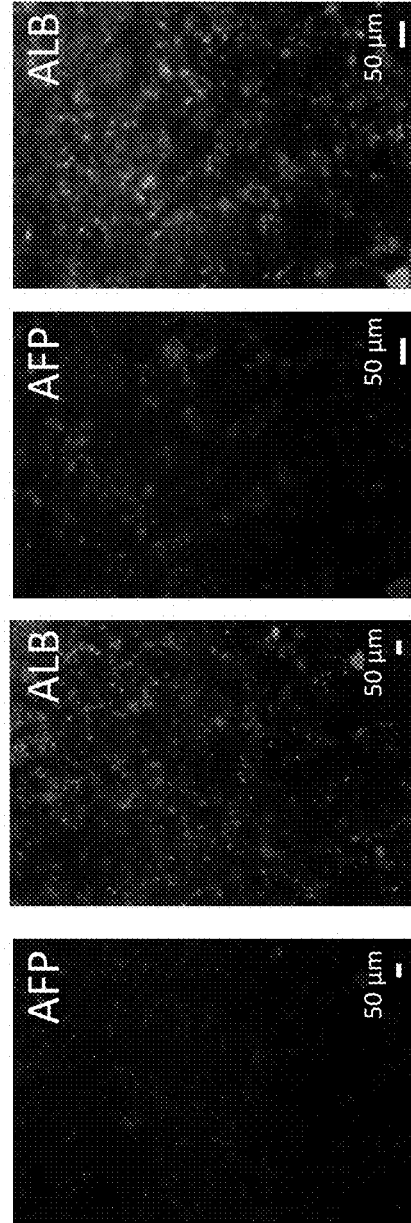

In FIG. 3A, a typical experimental procedure of the method of differentiating hPSCs into liver cells according to the present invention is illustrated.

(Results)

It was confirmed that the method of the present invention was able to achieve differentiation of hPSCs into liver cells rapidly (8 days), efficiently and homogeneously, and simply (only one time of treatment with the Sendai virus vector, and only one time of treatment with phosphospermine-siPOU5F1) with the two kinds of media (see FIG. 3B to FIG. 3E).

Example 4

(Differentiation into Hematopoietic Cells)

In this Example, it is confirmed that a temperature-sensitive Sendai virus vector expressing a human SPI1 gene can differentiate hPSCs into hematopoietic cells.

(Materials and Methods)

<Cell Culture>

An iPSC line derived from human adipose stem cells (iPSCs-ADSC) was obtained from System Biosciences (Palo Alto). Cells were maintained as undifferentiated pluripotent cells in accordance with a standard hPSC culture method involving using StemFit basic02 (Ajinomoto) supplemented with 100 ng/ml FGF2. The cells were cultured on a cell culture dish coated with lamin-511 (iMatrix-511, Nippi). For hematopoietic cell differentiation, α-MEM (Thermo-Fisher) supplemented with 5% KSR (Thermo-Fisher) was used as a culture medium.

<Sendai Virus Vector>

A temperature-sensitive Sendai virus vector expressing human SPI1 (SeV18+hSPI1/TS15ΔF) was custom-made by ID Pharma on contract. This Sendai virus vector is F protein-deficient, and hence is nontransmissible. This Sendai virus vector is temperature-sensitive, and this virus functions at 33° C. and is inactivated at 37° C. A stock solution of the Sendai virus vector was diluted to $1\times10^4$ CIU/μl.

<Phosphospermine-Bound siPOU5F1>

In order to suppress the expression of human POU5F1 in the hPSCs, small interfering RNAs (siRNAs) against human POU5F1 were designed and used. In order to introduce the siRNAs without using lipofection or any other cationic lipid-based transfection reagent, the siRNAs were bound with phosphospermine (Paris et al., Molecular Pharmaceutics 2012. 9: 3464-3475). Sequences used are a human POU5F1 sense strand: 5'-GCCCGAAAGAGAAAGCGAAdT*dT-3' (SEQ ID NO: 16) and a human POU5F1 antisense strand: 5'-UUCGC-UUUCUCUUUCGGGCdCdT-3' (SEQ ID NO: 17). The sense strand has 19 RNA bases and 2 DNA bases having added thereto 30 spermine molecules at the site indicated by *. The antisense strand has 19 RNA bases and 2 DNA bases. The sense strand and the antisense strand were annealed, and stored as a 100 μM stock solution.

<Procedure>

(1) On Day 1, the human iPSCs (iPSCs-ADSC line) are plated in a 24-well plate or a 4-well plate at $1.0\times10^5$ cells in 250 μl of the medium per well. The cell culture medium used is α-MEM (Thermo-Fisher) supplemented with 5% KSR (Thermo-Fisher). Immediately after the plating, the Sendai virus vector encoding the human SPI1 gene is added to the cell culture medium at a multiplicity of infection (MOI) of 2.5. In this Example, 25 μl of a Sendai virus solution containing $2.5\times10^5$ CIU is added to 250 μl of the medium containing $1.0\times10^5$ cells. One hour after the addition of the Sendai virus vector, 1 ml of a culture solution is added to a total amount of 1.275 ml per well. The cells are cultured in a $CO_2$ incubator at 33° C., a permissive temperature for viral replication and gene expression. The culture medium (1 ml/well) is changed daily.

(2) On Day 2, 4 μl of phosphospermine-siPOU5F1 (100 μM stock solution) is added to 1 ml of the medium per well at a final concentration of 400 nM.

(3) On Day 4, the temperature of the $CO_2$ incubator is changed to 37° C., a non-permissive temperature for viral replication and gene expression.

(4) On Day 6, the cells are fixed, and the efficiency of cell differentiation is evaluated using immunostaining. The immunostaining is performed by incubating the fixed cells using an anti-CD45 antibody.

(Results)

It can be confirmed that the method of the present invention can achieve differentiation of hPSCs into hematopoietic CD45-positive cells rapidly (5 days), efficiently and homogeneously, and simply (only one time of treatment with the Sendai virus vector, and only one time of treatment with phosphospermine-siPOU5F1).

Example 5

(Differentiation into Dopaminergic Neurons)

In this Example, it is confirmed that a temperature-sensitive Sendai virus vector expressing a human FOXA1 gene can differentiate hPSCs into dopaminergic neurons within 1 week.

(Materials and Methods)

<Cell Culture>

An iPSC line derived from human adipose stem cells (iPSCs-ADSC) was obtained from System Biosciences (Palo Alto). Cells were maintained as undifferentiated pluripotent cells in accordance with a standard hPSC culture method involving using StemFit basic02 (Ajinomoto) supplemented with 100 ng/ml FGF2. The cells were cultured on a cell culture dish coated with lamin-511 (iMatrix-511, Nippi).

For dopaminergic neuron differentiation, a 1:1 mixture of DMEM/F12 HAM and Neurobasal medium was used as a cell culture medium. The medium was supplemented with 1×N2/B27 (without vitamin A and retinoic acid), BDNF (20 ng/ml), GDNF (20 ng/ml), TGF-β3 (1 ng/ml), ascorbic acid (final concentration: 0.2 mM), and cAMP (final concentration: 0.5 mM).

<Sendai Virus Vector>

A temperature-sensitive Sendai virus vector expressing human FOXA1 (SeV18+hFOXA1/TS15ΔF) was custom-made by ID Pharma on contract. This Sendai virus vector is F protein-deficient, and hence is nontransmissible. This Sendai virus vector is temperature-sensitive, and this virus functions at 33° C. and is inactivated at 37° C. A stock solution of the Sendai virus vector was diluted to $1\times10^4$ CIU/μl.

<Procedure>

(1) On Day 1, the human iPSCs (iPSCs-ADSC line) are plated in a 24-well plate or a 4-well plate at $1.0\times10^5$ cells in 250 μl of the medium per well. The above-mentioned culture medium is used (1:1 mixture of DMEM/F12 HAM and Neurobasal medium supplemented with 1×N2/27, BDNF, GDNF, TGF-β3, ascorbic acid, and cAMP). Immediately after the plating, the Sendai virus vector encoding the human FOXA1 gene is added to the cell culture medium at a multiplicity of infection (MOI) of 2.5. In this Example, 25 μl of a Sendai virus solution containing $2.5\times10^5$ CIU is added to 250 μl of the medium containing $1.0\times10^5$ cells. One hour after the addition of the Sendai virus vector, 1 ml of a culture solution is added to a total amount of 1.275 ml per well. The cells are cultured in a $CO_2$ incubator at 33° C., a permissive temperature for viral replication and gene expression. The culture medium (1 ml/well) is changed daily.
(2) On Day 3, the temperature of the $CO_2$ incubator is changed to 37° C., a non-permissive temperature for viral replication and gene expression.
(3) As an optional procedure, on Day 4, the cells are passaged, and cultured on an ornithine/laminin-coated glass coverslip so that differentiated neurons are easily visible under a microscope.
(4) On Day 6, the cells are fixed, and the efficiency of cell differentiation is evaluated using immunostaining. The immunostaining is performed by incubating the fixed cells overnight using an anti-tubulin (3 (TUBB3) antibody and tyrosine hydroxylase (TH).

(Results)

It is confirmed that the method of the present invention can achieve differentiation of hPSCs into TH-positive dopaminergic neurons rapidly (5 days), efficiently and homogeneously, and simply (only one time of treatment with the Sendai virus vector).

According to the present invention, the method of inducing differentiation of a pluripotent stem cell into a desired cell type within a short period of time and with high efficiency can be provided.

What is claimed is:

1. A method of differentiating a pluripotent stem cell into a desired cell type, comprising:
   a) adding a Sendai virus vector encoding a transcription factor required for induction of differentiation into the desired cell type to a pluripotent stem cell in a cell culture medium; and
   b) culturing the pluripotent stem cell to differentiate the pluripotent stem cell into the desired cell, wherein the desired cell type is a motor neuron, the transcription factor comprises NEUROG3, and an efficiency of the differentiating into the motor neuron is from about 76% to about 90%.

2. The method according to claim 1, wherein the Sendai virus vector is temperature-sensitive.

3. The method of claim 2, wherein the culturing the pluripotent stem cell to differentiate the pluripotent stem cell into the desired cell comprises culturing the pluripotent stem cell at a first temperature where the Sendai virus vector is activated and then culturing the pluripotent stem cell at a second temperature where the Sendai virus vector is deactivated, and wherein the first temperature is lower than the second temperature.

4. The method of claim 1, wherein NEUROG3 is the sole transcription factor for the differentiation into the motor neuron.

* * * * *